(12) United States Patent
Aarabi et al.

(10) Patent No.: US 12,672,845 B2
(45) Date of Patent: Jul. 7, 2026

(54) SYSTEM AND METHOD FOR MEASURING TOTAL BLOOD VOLUME WITH ULTRASOUND

(71) Applicant: UNIVERSITY OF WASHINGTON, Seattle, WA (US)

(72) Inventors: Shahram Aarabi, Seattle, WA (US); Daniel F. Leotta, Seattle, WA (US)

(73) Assignee: University of Washington, Seattle, WA (US)

( * ) Notice: Subject to any disclaimer, the term of this patent is extended or adjusted under 35 U.S.C. 154(b) by 44 days.

(21) Appl. No.: 18/259,388

(22) PCT Filed: Dec. 20, 2021

(86) PCT No.: PCT/US2021/064352
§ 371 (c)(1),
(2) Date: Jun. 26, 2023

(87) PCT Pub. No.: WO2022/140259
PCT Pub. Date: Jun. 30, 2022

(65) Prior Publication Data
US 2024/0057968 A1 Feb. 22, 2024

Related U.S. Application Data

(60) Provisional application No. 63/129,142, filed on Dec. 22, 2020.

(51) Int. Cl.
*A61B 8/08* (2006.01)
*A61B 8/00* (2006.01)

(52) U.S. Cl.
CPC .......... *A61B 8/0891* (2013.01); *A61B 8/4488* (2013.01); *A61B 8/486* (2013.01); *A61B 8/5223* (2013.01)

(58) Field of Classification Search
None
See application file for complete search history.

(56) References Cited

U.S. PATENT DOCUMENTS

| | | |
|---|---|---|
| 4,257,278 A | 3/1981 | Papadofrangakis |
| 5,235,985 A | 8/1993 | McMorrow |

(Continued)

OTHER PUBLICATIONS

Wunsch H, Wagner J, Herlim M, Chong DH, Kramer AA, Halpern SD. ICU occupancy and mechanical venAlator use in the United States. Crit Care Med 2013;41:2712-9.

(Continued)

*Primary Examiner* — Jonathan Cwern
(74) *Attorney, Agent, or Firm* — CHRISTSEN O'CONNOR JOHNSON KINDNESS PLLC

(57) ABSTRACT

Apparatuses and methods for measuring total blood volume with ultrasound are disclosed. In one embodiment, a system for monitoring a blood volume of a patient includes an ultrasound transmitter configured for emitting an ultrasound toward a target blood vessel of the patient; and an ultrasound receiver configured for receiving the ultrasound reflected from the target blood vessel of the patient. The system also includes, a controller configured for: determining an expanded state of the blood vessel based on the ultrasound reflected from the target blood vessel; determining a collapsed stated of the blood vessel based on the ultrasound reflected from the target blood vessel; and determining the blood volume of the patient based on the ratio of the collapsed stated and the expanded stated of the blood vessel.

18 Claims, 17 Drawing Sheets

(56) References Cited

U.S. PATENT DOCUMENTS

| | | | | |
|---|---|---|---|---|
| 5,505,204 | A | 4/1996 | Picot | |
| 5,515,856 | A * | 5/1996 | Olstad | G01S 15/8993 |
| | | | | 600/440 |
| 9,357,980 | B2 | 6/2016 | Toji | |
| 9,731,066 | B2 | 8/2017 | Liu | |
| 2003/0114756 | A1 | 6/2003 | Li | |
| 2004/0191199 | A1 | 9/2004 | Mougin | |
| 2005/0251039 | A1* | 11/2005 | Chalana | G01S 15/8993 |
| | | | | 600/437 |
| 2010/0145197 | A1* | 6/2010 | Stapf | A61B 8/4488 |
| | | | | 382/128 |
| 2011/0152651 | A1 | 6/2011 | Berkow | |
| 2012/0089020 | A1 | 4/2012 | Nitta | |
| 2013/0303915 | A1* | 11/2013 | Barnard | A61B 8/5207 |
| | | | | 600/449 |
| 2014/0031688 | A1* | 1/2014 | Perrey | A61B 8/54 |
| | | | | 600/443 |
| 2015/0216506 | A1* | 8/2015 | Chang | G01S 7/52071 |
| | | | | 345/419 |
| 2016/0029972 | A1 | 2/2016 | Lenehan | |
| 2016/0183885 | A1 | 6/2016 | Hu | |
| 2017/0080255 | A1 | 3/2017 | Law | |
| 2017/0296140 | A1 | 10/2017 | Ebbini | |
| 2018/0177486 | A1 | 6/2018 | Gifford, III et al. | |
| 2018/0317881 | A1 | 11/2018 | Astigarraga | |
| 2020/0253583 | A1 | 8/2020 | Brisken et al. | |
| 2021/0113194 | A1* | 4/2021 | Padwal | G06T 7/0012 |

OTHER PUBLICATIONS

Hall MJ, Schwartzman A, Zhang J, Liu X. Ambulatory Surgery Data From Hospitals and Ambulatory Surgery Centers: United States, 2010. Natl Health Stat Report 2017:1-15.

Saran R, Robinson B, AbboW KC, et al. US Renal Data System 2017 Annual Data Report: Epidemiology of Kidney Disease in the United States. Am J Kidney Dis 2018;71:A7.

Virani SS, Alonso A, Benjamin EJ, et al. Heart Disease and Stroke StaAsAcs-2020 Update: A Report From the American Heart AssociaAon. CirculaAon 2020;141:e139-e596.

Kalantari K, Chang JN, Ronco C, Rosner MH. Assessment of intravascular volume status and volume responsiveness in criAcally ill paAents. Kidney Int 2013;83:1017-28.

Mackenzie DC, Noble VE. Assessing volume status and fluid responsiveness in the emergency department. Clin Exp Emerg Med 2014;1:67-77.

Schindler AW, Marx G. Evidence-based fluid management in the ICU. Curr Opin Anaesthesiol 2016;29:158-65.

Van der Mullen J, Wise R, Vermeulen G, Moonen PJ, Malbrain M. Assessment of hypovolaemia in the criAcally ill. Anaesthesiol Intensive Ther 2018;50:141-9.

Kidney X Redesign Dialysis Prize CompeAAon. (Accessed Oct. 20, 2020, at hWps://www.kidneyx.org/prizecompeAAons/RedesignDialysisPhaseII.).

NHLBI Catalyze Program. (Accessed Oct. 20, 2020, at hWps://www.nhlbi.nih.gov/grants-and-training/funding-opportuniAes-and-contacts/NHLBI-Catalyze-Program.).

Scientific Program Areas of the NIDDK. (Accessed Oct. 20, 2020, at https://sbir.nih.gov/niddk/divisions.).

Bridges E, Hatzfeld JJ. Noninvasive ConAnuous Hemoglobin Monitoring in Combat CasualAes: A Pilot Study. Shock 2016;46:55-60.

Sanders, S. et al. Harvard Business Review: How to Make Remote Monitoring Tech Part of Everyday Health Care. (Accessed Oct. 20, 2020, at https://hbr.org/2020/07/how-to-make-remote-monitoring-tech-part-of-everyday-health-care.).

Hofmann R, Voller H, Nagels K, et al. First outline and baseline data of a randomized, controlled mulAcenter trial to evaluate the health economic impact of home telemonitoring in chronic heart failure—CardioBBEAT. Trials 2015;16:343.

Rosner MH, Lew SQ, Conway P, et al. PerspecAves from the Kidney Health IniAaAve on Advancing Technologies to Facilitate Remote Monitoring of PaAent Self-Care in RRT. Clin J Am Soc Nephrol 2017;12:1900-9.

Grustam AS, Buyukkaramikli N, Koymans R, Vrijhoef HJM, Severens JL. Value of informaAon analysis in telehealth for chronic heart failure management. PLoS One 2019;14:e0218083.

Dipiti A., et al., "Role of inferior vena cava diameter in assessment of volume status: a meta-analysis." Am J Emerg Med 2012;30:1414-9 e1.

Prekker M. E. et al., "Point-of-Care Ultrasound to Estimate Central Venous Pressure: A Comparison of Three Techniques*" Crit Care Med 2013;41:833-41.

Guarracino F. et al., "Jugular vein distensibility predicts fluid responsiveness in septic patients." Crit Care 2014; 18:647.

Pourmand, A. et al., "The utility of point-of-care ultrasound in the assessment of volume status in acute and critically ill patients," World J Emerg Med, vol. 10, No. 4, 2019, 232-238.

"Non-invasive Hemodynamic Monitoring During Blood Donation for DevelopingModels of Early Blood Loss" (Accessed Oct. 20, 2020, at https://clinicaltrials.gov/ct2/show/NCT01448694.).

Global Hemodynamic Monitoring Systems Market 2020 Current and Future Market Landscape Analysis 2026. (Accessed Oct. 20, 2020, at https://www.marketwatch.com/press-release/global-hemodynamic-monitoring-systems-market-2020-current-and-future-market-landscape-analysis-2026-2020-08-18.).

North America Dialysis Market to surpass USD 37.5 Billion by 2026. (Accessed Oct. 20, 2020, at https://www.globenewswire.com/news-release/2020/07/16/2063141/0/en/North-America-Dialysis-Market-to-surpass- USD-37-5-Billion-by-2026.html.).

CDC Chronic Kidney Disease (CKD) Surveillance System. (Accessed Oct. 10, 2020, at https://nccd.cdc.gov/ckd/.).

Arnaout RC, L; Zhao, Y; Levine, J; Chinn, E; Moon-Grady, A. Expert-level prenatal detection of complex congenital heart disease from screening ultrasound using deep learning. medRxiv 2020.

Rudski LG, Lai WW, Afilalo J, et al. Guidelines for the echocardiographic assessment of the right heart in adults: a report from the American Society of Echocardiography endorsed by the European Association of Echocardiography, a registered branch of the European Society of Cardiology, and the Canadian Society of Echocardiography. J Am Soc Echocardiogr 2010;23:685-713; quiz 86-8.

Ferrada P, Evans D, Wolfe L, et al. Findings of a randomized controlled trial using limited transthoracic echocardiogram (LTTE) as a hemodynamic monitoring tool in the trauma bay. J Trauma Acute Care Surg 2014;76:31-7; discussion 7-8.

Madani A, Arnaout R, Mofrad M, Arnaout R. Fast and accurate view classification of echocardiograms using deep learning. NPJ Digit Med 2018;1.

Norgeot B, Quer G, Beaulieu-Jones BK, et al. Minimum information about clinical artificial intelligence modeling: the MI-CLAIM checklist. Nat Med 2020;26:1320-4.

Sengupta PP, Shrestha S, Berthon B, et al. Proposed Requirements for Cardiovascular Imaging-Related Machine Learning EvaluaAon (PRIME): A Checklist: Reviewed by the American College of Cardiology Healthcare Innovation Council. JACC Cardiovasc Imaging 2020;13:2017-35.

White NJ, Wang X, Bradbury N, et al. Fluid resuscitation of uncontrolled hemorrhage using a hemoglobin-based oxygen carrier: effect of traumautic brain injury. Shock 2013;39:210-9.

White NJ, Wang X, Liles C, Stern S. Fibrinogen concentrate improves survival during limited resuscitation of uncontrolled hemorrhagic shock in a Swine model. Shock 2014;42:456-63.

White NJ, Mehic E, Wang X, et al. Rediscovering the wound hematoma as a site of hemostasis during major arterial hemorrhage. J Thromb Haemost 2015;13:2202-9.

Finnerty NM, Panchal AR, Boulger C, et al. Inferior Vena Cava Measurement with Ultrasound: What Is the Best View and Best Mode?. West J Emerg Med. 2017;18(3):496-501. doi:10.5811/westjem.2016.12.32489—"Standardization and optimal techniques for IVC assessment have yet to be agreed upon.".

Halpern NA, Pastores SM. Critical care medicine in the United States 2000-2005: an analysis of bed numbers occupancy rates, payer mix, and costs. Crit Care Med. 2010; 38(1):65-71.

$36.13Bn Patient MonitoringSolutions Market Study, 2019-2028:Data on Hemodynamic, Cardiac, Respiratory, Neuromonitoring, Diabetes, and TemperatureMonitoring Devices, 2019-2028:

(56) References Cited

OTHER PUBLICATIONS

Data on Hemodynamic, Cardiac, Respiratory, Neuromonitoring, Diabetes, and Temperature Monitoring Devices. (Accessed Oct. 20, 2020, at https://www.prnewswire.com/news-releases/36-13bn-paAent-monitoring-soluAons-market-study-2019-2028-data-on-hemodynamic-cardiac-respiratory-neuromonitoring-diabetes-and-temperature-monitoring-devices-300981546.html.).

Beigel, R. M.D. et al., "Noninvasive Evaluation of Right Atrial Pressure," JASE. 2013;26(9): 1033-42.

Mansfield, P. F. M.D. et al., "Complications and Failures of Subclavian-Vein Catheterization," N Eng J Med. 1994;331:1735-38.

Merrer, J. M.D. et al., "Complications of Gemoral and Subclavian Venous Catheterization in Critically Ill Patients: A Radomized Controlled Trial," JAMA. 2001;286: 700-07.

Lorente, L. et al., "Central venous catheter-related infection in a prospective and observational study of 2,595 catheters," Crit Care. 2005;9:R631-35.

Xing, C-Y, MD et al., "New Method for Noninvasive Quantification of Central Venous Pressure by Ultrasound," Circ: Cardio Imag. 2015;8(5):e003085.

Ogum, C. et al., "Non-invasive central venous pressure estimation by ultrasoundguided internal jugular vein cross-sectional area measurement," Biomed Phys Eng Express. 2016;2:025004.

Lipton. B., MD, RDMS, "Estimation of Central Venous Pressure by Ultrasound of the Internal Jugular Vein," Am J Emerg Med. 2000;18(4):432-4.

Cardiovascular Ultrasound Market Size, Share & Trends Analysis ReportBy Technology (Doppler, 3/4D), By Display (Color, B/W), By End-use(Hospitals, Ambulatory Care Centers), By Type, And Segment Forecasts,2023-2030; 2018-2025. ResearchandMarkets. com. Nov. 13, 2018.

Global Cardiovascular Ultrasound System Market Trends, Analysis, Growth and Forecast: 2018 to 2027. MarketResearch.biz. Aug. 2, 2018.

Hospital Utilization (in non-Federal short-stay hospitals); National Center for Health Statistics; CDC <https://www.cdc.gov/nchs/fastats/hospital.htm>.

Emergency Department Visits; National Center for Health Statistics; CDC <https://www.cdc.gov/nchs/fastats/emergency-department. htm>.

Huang, Q. and Z. Zeng, "A Review on Real-Time 3D Ultrasound Imaging Technology," Hindawi; BioMed Research International; vol. 2017, Article ID 6027029, 20 pages <https://doi.org/10.1155/2017/6027029>.

Correia, M. et al., "4D ultrafast ultrasound flow imaging: in vivo quantification of arterial volumetric flow rate in a single heartbeat," Phys. Med. Biol. 61 L48.

International Search Report and Written Opinion mailed on Mar. 9, 2022, issued in corresponding International App. No. PCT/US2021/064352, filed on Dec. 20, 2021, 9 pages.

Nickerson, C., "The Dark Art of IVC Ultrasound, "LITFL—CCC <https://litfl.com/the-dark-art-of-ivc-ultrasound/>.

Extended European Search Report mailed Oct. 14, 2024, issued in corresponding European Application No. 21911974.0, filed Dec. 20, 2021, 8 pages.

* cited by examiner

CAROTID / JUGULAR : INHALE

CAROTID / JUGULAR : EXHALE

*NORMAL PHYSIOLOGY*
*LIMITED VARIATION WITH RESPIRATION*

% CHANGE
IN VOLUME

EXPIRATION

INSPIRATION

*LOW INTRAVASCUAR VOLUME PHYSIOLOGY*
*INCREASED VARIATION WITH RESPIRATION*

% CHANGE
IN VOLUME

EXPIRATION

INSPIRATION

2D IMAGE PLANE (SLICE)

DEPTH VS. TIME

SYSTEM AND METHOD FOR MEASURING TOTAL BLOOD VOLUME WITH ULTRASOUND

CROSS-REFERENCE(S) TO RELATED APPLICATION(S)

This application is a National Stage of International Application No. PCT/US2021/064352, which claims the benefit of Provisional Application No. 63/129,142, filed Dec. 22, 2020, which is incorporated herein by reference.

BACKGROUND

There is currently no accepted method for determining volume of blood circulating inside the patient's body or fluid status/responsiveness of critically ill patients. Therefore, in many cases it is not readily known whether the patient needs a transfusion or infusion, and, if so, what quantities of additional fluids are needed.

With no current availability of a non-invasive system to measure a patient's circulating blood volume or fluid status/responsiveness, an estimated 141 million patients a year are treated in emergency rooms, 5.7 million patients a year are admitted to intensive care units, and 27 million patients undergo major surgery in the US every year while being potentially affected by this gap. Additionally, patients suffering from sepsis or undergoing dialysis are affected by this technological gap.

Studies have made claims correlating an observed condition of the inferior vena cava (IVC), (e.g., diameter of the IVC) to a general condition of the patient (e.g., blood pressure, total blood volume, etc.), but these claims have been subject to skepticism ranging from measurement methodology to measurement reliability for different patient condition (e.g., different populations may have different IVC baselines and responses). Point of care IVC ultrasound has been used for understanding blood level in patients. However, these conventional technologies require a skilled sonographer and image interpretation to properly estimate the blood level in patients.

Repeatable and efficient data gathering is needed to generate robust information that supports critical decisions during the course of patient care. Accordingly, systems and methods are needed for improved determination of volume of blood circulating inside the patient's body and other bodily fluid status of patients, especially with the critically ill patients.

SUMMARY

This summary is provided to introduce a selection of concepts in a simplified form that are further described below in the Detailed Description. This summary is not intended to identify key features of the claimed subject matter.

Briefly, the inventive technology is directed to a non-invasive determination of patient's circulating blood volume or other fluid levels of the patient. It is known that about 70% of blood is stored in the veins of the patient. Therefore, in some embodiments of the present invention, the estimates of the total blood volume of the patient are based on the behavior of inferior vena cava (IVC).

In some embodiments, an ultrasound probe (e.g., an ultrasound transceiver) may be attached to patient's body. The ultrasound scanner may detect the target vein (e.g., IVC) even if the ultrasound scanner is imprecisely or approximately positioned on the patient's body. In operation, the ultrasound scanner acquires images of different states of expansion of the target vein, ranging from a fully expanded state (maximum IVC diameter) to a fully reduced state (minimum IVC diameter, also referred to as a collapsed state of IVC). Generally, timing of the fully expanded state and collapsed state of the IVC relates to patient's breathing cycle: the maximum diameter state corresponding to the expiration state, and the minimum diameter corresponding to the inspiration state of patient's breathing cycle. Therefore, in some embodiment, acquisition of images may be synchronized with patient's breathing cycle.

In some embodiments, the acquired images are automatically interpreted to determine a ratio of minimum and maximum diameters of patient's IVC without determining a true 3D shape or a volume of the IVC at its expanded/collapsed state. In other embodiments, the acquired images are interpreted to reconstruct the 3D shape of patient's IVC, followed by determination of a ratio of minimum and maximum diameters or volumes of the IVC at its expanded/collapsed states. Such minimum/maximum diameter ratio may be referred to as "collapsibility" or change in volume of the IVC, which can be expressed as a percentage.

Generally, higher values of the change in volume (higher collapsibility) indicate that a patient is experiencing a deficit of blood thus indicating higher urgency of blood transfusion or fluid infusion. In many embodiments, severity of IVC collapsibility is assessed automatically based on a predetermined threshold value, and without needing a highly qualified technician or physician to interpret images. For example, IVC collapsibility may be determined using known mathematical algorithms or artificial intelligence that evaluates geometrical shapes. In some embodiments, the ratio of minimum to maximum diameter may be determined without reconstructing a full 3D shape of the IVC in either of its minimum or maximum diameter states.

In some embodiment, the ultrasound images may be based on ultrasound M-mode (motion mode). With the ultrasound M-mode, the ultrasound data may be formatted to determine movement of the wall of the vessel (e.g., wall of the IVC) within one breathing cycle. Based on such movement of the wall of the vessel, collapsibility of the vessel can be determined, leading to the above-explained determination of the blood level in the patient.

In operation, the ultrasound probe (e.g., a transceiver) may emit ultrasound toward a generally known, but imprecisely understood location of the IVC. The ultrasound probe may transmit ultrasound in several directions that are generated by, for example, phased array ultrasound transmitter (1D phased array, 1D curved array, or 2D matrix array) or a single-element ultrasound transmitter. Reflected ultrasound signal received by the receiver may be processed by a computer or controller such that the motion of the IVC is detected and the value of the IVC collapsibility is determined.

In one embodiment, a system for monitoring a blood volume of a patient includes: an ultrasound transmitter configured for emitting an ultrasound toward a target blood vessel of the patient; and an ultrasound receiver configured for receiving the ultrasound reflected from the target blood vessel of the patient. The system also includes a controller configured for: determining an expanded state of the blood vessel based on the ultrasound reflected from the target blood vessel; determining a collapsed state of the blood vessel based on the ultrasound reflected from the target blood vessel; determining a ratio of the collapsed state and the expanded state of the blood vessel; and determining the blood volume of the patient based on the ratio of the collapsed state and the expanded state of the blood vessel.

In one aspect, determining the expanded state of the blood vessel is synchronized with an expiration cycle of patient's breathing, and the determining of the collapsed state of the blood vessel is synchronized with an inspiration cycle of the patient's breathing.

In one aspect, the controller is further configured for determining whether the patient requires a blood transfusion.

In another aspect, the determining whether the patient requires the blood transfusion is based on the ratio of the collapsed state and the expanded state of the blood vessel being below a predetermined threshold.

In one aspect, the blood vessel is an inferior vena cava (IVC).

In one aspect, the determining the expanded state of the blood vessel and the determining of the collapsed state of the blood vessel is performed without determining a 3D shape of the blood vessel.

In one aspect, the ultrasound is transmitted toward the target blood vessel in a plurality of rotational planes or tilt planes.

In one aspect, the ultrasound transmitter is a phased array ultrasound transmitter.

In one aspect, the controller is further configured for generating a 4D M-mode image of the blood vessel.

In another aspect, the controller is further configured for extracting 2D image slices from the 4D M-mode images.

In one aspect, the 2D image slices are extracted along a time axis of the 4D M-mode images.

In one embodiment, a method for monitoring a blood volume of a patient, the method including: emitting an ultrasound toward a target blood vessel of the patient by an ultrasound transmitter; receiving the ultrasound reflected from the target blood vessel of the patient by an ultrasound receiver; determining an expanded state of the blood vessel based on the ultrasound reflected from the target blood vessel; determining a collapsed state of the blood vessel based on the ultrasound reflected from the target blood vessel; determining a ratio of the collapsed state and the expanded state of the blood vessel; and determining the blood volume of the patient based on the ratio of the collapsed state and the expanded state of the blood vessel.

In one aspect, the method also includes: synchronizing the determining the expanded state of the blood vessel with an expiration cycle of patient's breathing, and synchronizing the determining of the collapsed state of the blood vessel with an inspiration cycle of the patient's breathing.

In another aspect, the method also includes determining whether the patient requires a blood transfusion based on the ratio of the collapsed state and the expanded state of the blood vessel being below a predetermined threshold.

In one aspect, the determining the expanded state of the blood vessel and the determining of the collapsed state of the blood vessel is performed without determining a 3D shape of the blood vessel.

In one aspect, the ultrasound is transmitted toward the target blood vessel in a plurality of rotational planes or tilt planes by the ultrasound transmitter that is a phased array ultrasound transmitter.

In one aspect, the method includes generating a 4D M-mode image of the blood vessel.

In another aspect, the method also includes extracting 2D image slices from the 4D M-mode images.

In one aspect, the 2D image slices are extracted along a time axis of the 4D M-mode images.

4

DESCRIPTION OF THE DRAWINGS

The foregoing aspects and many of the attendant advantages of the inventive technology will become more readily appreciated as the same are understood with reference to the following detailed description, when taken in conjunction with the accompanying drawings, wherein.

DETAILED DESCRIPTION

While several embodiments have been illustrated and described, it will be appreciated that various changes can be made therein without departing from the spirit and scope of the claimed subject matter.

Figure 1:
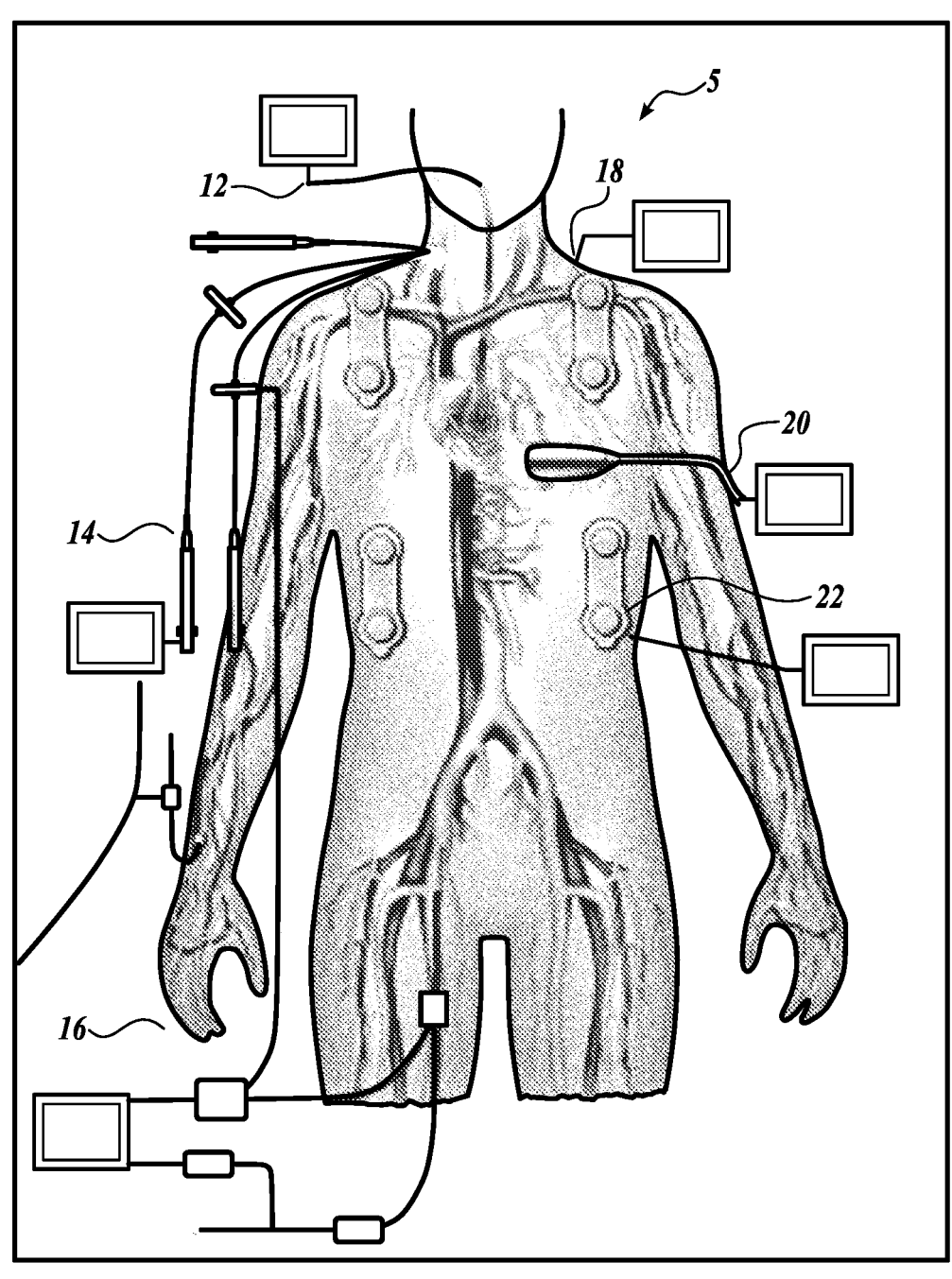
FIG. 1 is a schematic diagram of blood level measurements in accordance with prior art.

FIG. 1 is a schematic diagram of blood level measurements in accordance with prior art. Conventional blood level estimates rely on a set of measurements, each generally requiring a high level of medical or diagnostics expertise for interpreting the results. For example, conventional measurements can include an esophageal transesophageal echocardiogram (TEE) probe 12 that is inserted down the esophagus of the patient. Such ultrasound measurements offer an advantage of a clearer image of the heart because the ultrasound waves do not have to pass through skin, muscle, or bone tissue. In other situations, a standard trans-abdominal study is used as a conventional measurement for IVC imaging.

Furthermore, the conventional measurements may include a LiDCO monitor 14 that analyses blood pressure waveform to help with fluid management of high-risk surgical and critically ill patients. The conventional measurements may also include a Pulse Contour Cardiac Output (PiCCO) monitor 16. The PiCCO monitoring enables assessment of the patient's hemodynamic status to guide fluid therapy. A Swan-Ganz catheterization 18 (also called a right heart catheterization or a pulmonary artery catheterization) includes passing of a thin tube (catheter) into the right side of the heart and arteries leading to the lungs. Swan-Ganz catheter monitors heart's function and also blood flow and pressures in and around the heart. Echocardiography 20 may also be used for understanding blood level of the patients. This method uses sound waves to create moving pictures of the heart. Another diagnostics method used for hemodynamic monitoring in a clinical setting may be a non-invasive cardiac output monitor (NICOM) 22.

In general, several of the above conventional methods may be combined for an improved diagnostics of patient's fluid level. However, even when considered individually, the above conventional methods require a relatively high level of medical and diagnostic expertise to operate and to properly interpret results.

Figure 2:
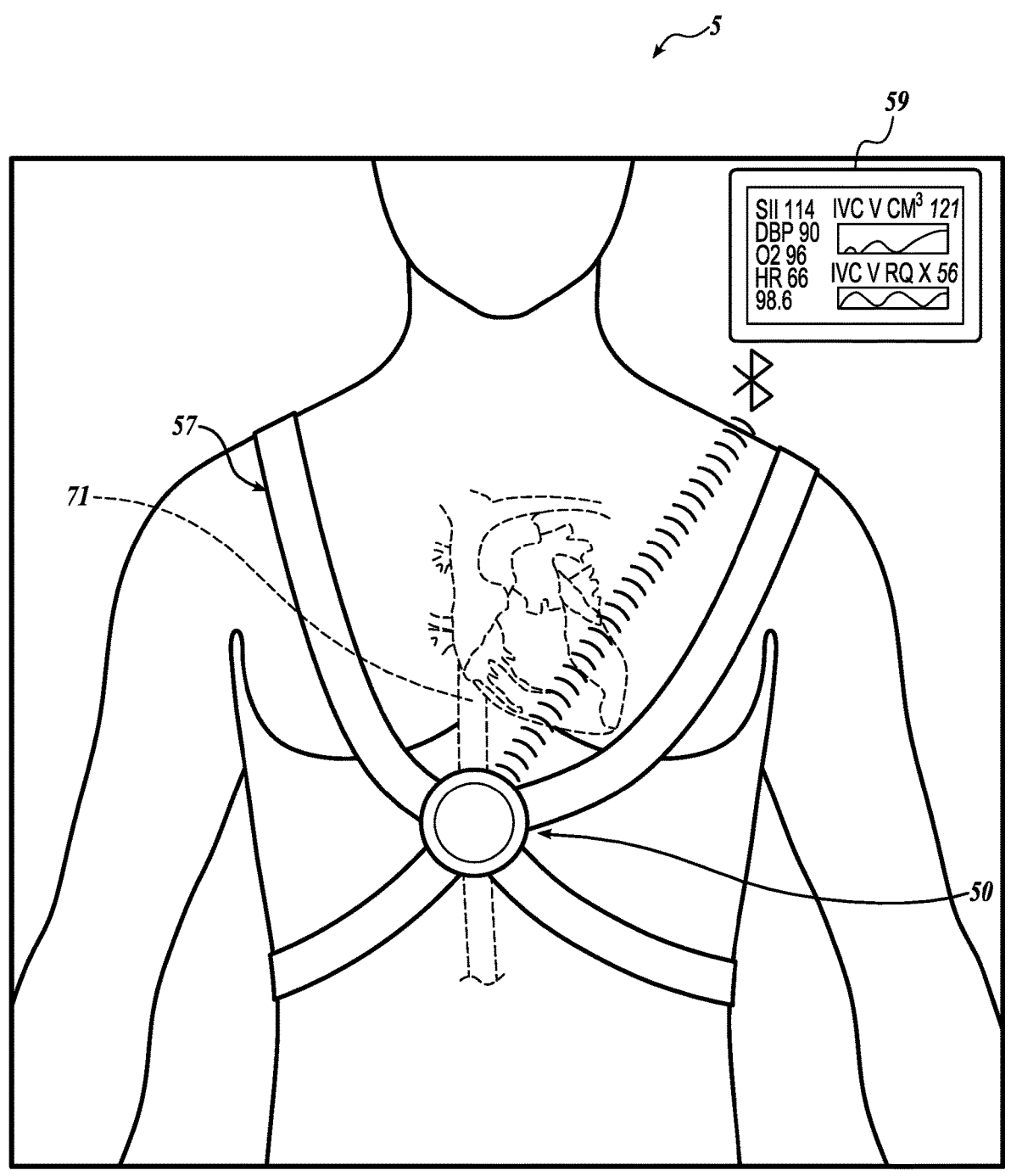
FIG. 2 is a schematic diagram of an ultrasound system in operation in accordance with an embodiment of the present technology.

FIG. 2 is a schematic diagram of an ultrasound system in operation in accordance with an embodiment of the present technology. In some embodiments, an ultrasound probe (also referred to as a scanhead, ultrasound transceiver, or ultrasound transmitter) 50 is attached to a patient 5.

A harness 57 may couple the ultrasound probe 50 to the patient in a specific location. In different embodiments, suitable attachment locations for the ultrasound probe 50 may be the patient's side (e.g., between ribs) viewing the IVC generally in the sagittal plane, the subxiphoid, neck, groin, or others suitable for a particular vessel being observed. In other embodiments for the IVC, the location of the ultrasound probe 50 placement is at the bottom of the patient's rib cage, where the probe may be pressed toward the patient's diaphragm and aimed, generally, directly into the patient, toward the IVC.

Some embodiments of inventive technology may rely on a customized ultrasound probe 50, which has a flatter profile than the conventional handheld probes. For example, a disc-shaped casing of the ultrasound probe 50 further simplifies coupling of the probe to the patient, because a force applied orthogonally to the patient is more easily applied at the flat backside of the probe. The custom probe also keeps the working area around the patient less obstructed if the patient continues to receive care while undergoing the IVC measurement. Once the probe 50 is fitted, generally no further operator involvement is needed for the IVC measurements. The resulting ultrasound images may be observable on a display 59.

Figure 3:
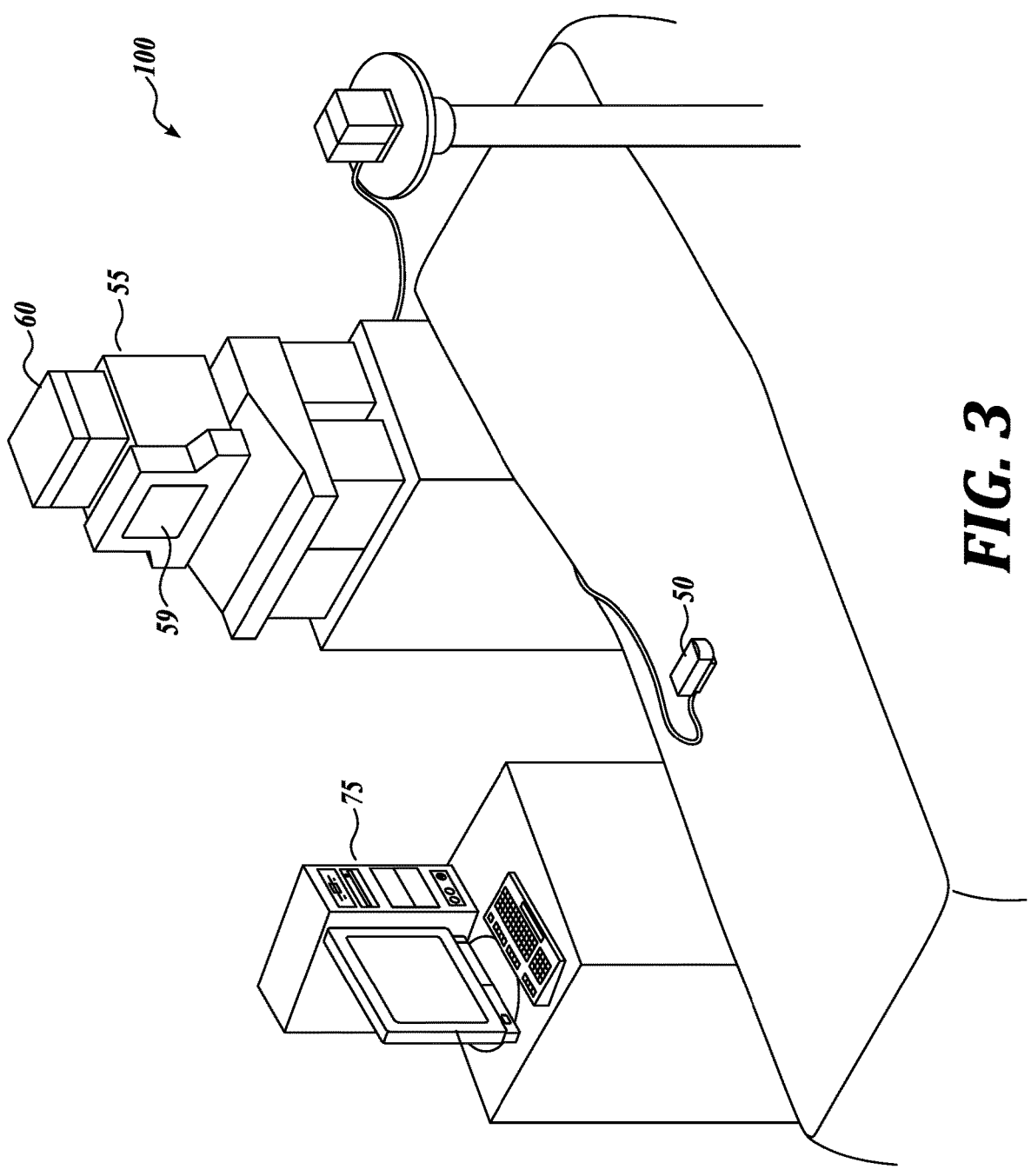
FIG. 3 is an isometric diagram of an ultrasound system in accordance with an embodiment of the present technology.

FIG. 3 is an isometric diagram of an ultrasound system 100 in accordance with an embodiment of the present technology. In some embodiments, the system 100 may be used for gathering 2D scans together with position and orientation of the ultrasound probe, thus enabling subsequent interpretation of the ultrasound images. System 100 may include the ultrasound probe 50, an ultrasound scanner 55 and 3D tracker electronics 60. In some embodiments, knowledge of the locations of the 2D image planes (whether by 3D tracking or mechanical scanning) can be used to produce 3D reconstructions of the vessel geometry. Operation of the system 100 may be controlled by a computer (also referred to as a personal computer, a controller, or a smart device) 75.

Figure 4:
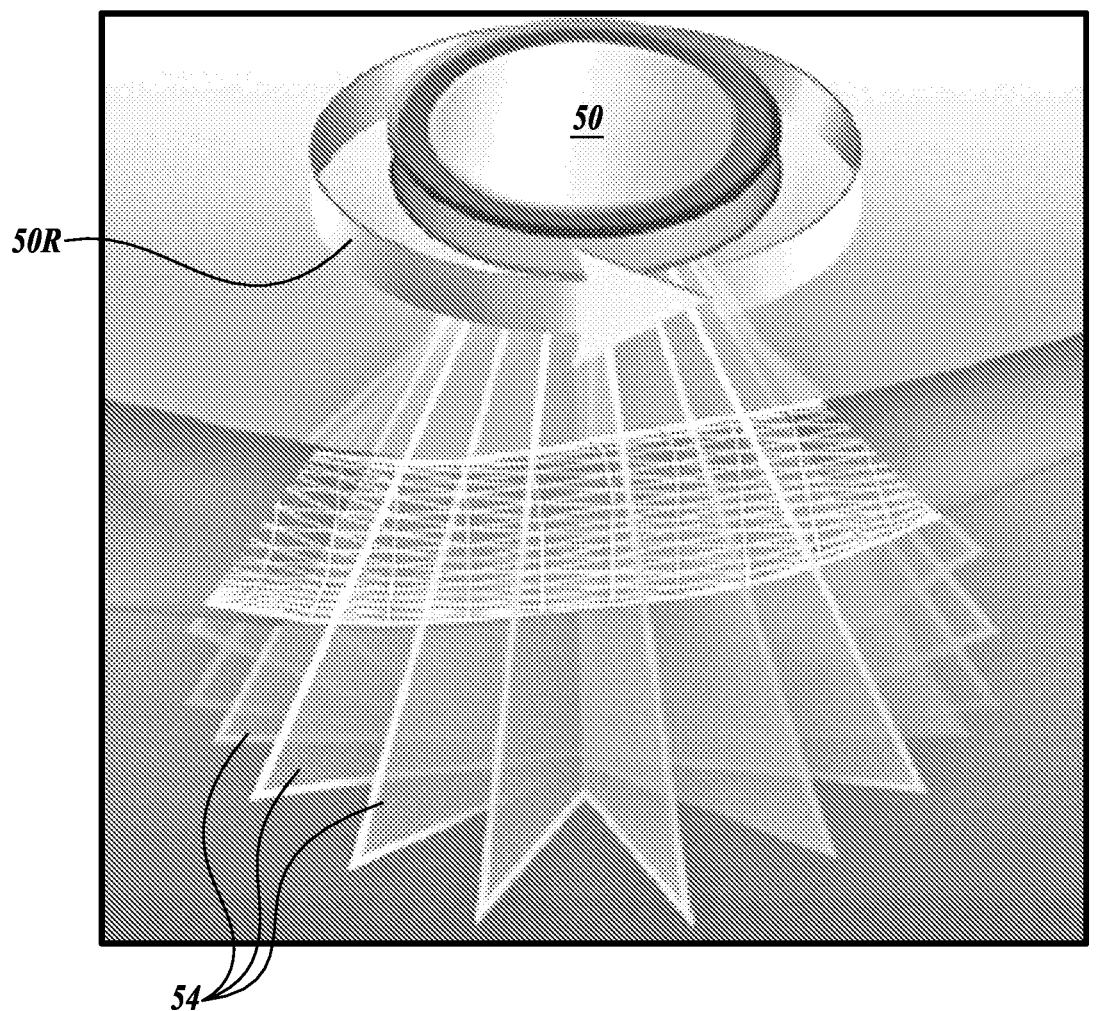
FIG. 4 is an isometric view of an ultrasound probe in operation in accordance with an embodiment of the present technology.

FIG. 4 is an isometric view of an ultrasound probe 50 in operation in accordance with an embodiment of the present technology. The ultrasound probe 50 may be physically rotated to generate and transmit ultrasound planes 54 in a rotational direction 50R. In some embodiments, the ultrasound probe 50 is a phased array or a matrix phased array ultrasound transducer that allows electronic steering of the ultrasound imaging planes in, for example, rotational direction 50R or in a tilt direction. Such steering of the ultrasound imaging planes may be helpful in overcoming imaging obstacles (e.g., by steering between ribs, or by scanning a larger area for the IVC rather than only scanning within a depth underneath the ultrasound probe). When operating as a transceiver, the ultrasound probe 50 is also capable of acquiring the reflected ultrasound images. As explained above, the known 2D image plane coordinates from the mechanical scan can be used to create a 3D reconstruction of the vessel geometry.

Figure 5A:
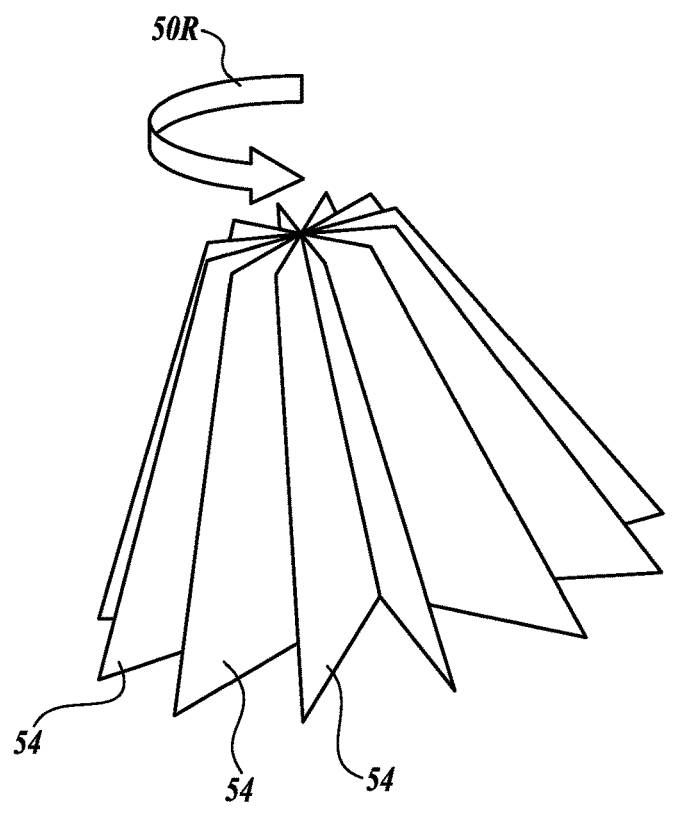
FIGS. 5A, 5B and 5C show imaging ultrasound planes in several rotation and tilt angles, and in a combination of rotation and tilt angles in accordance with an embodiment of the present technology.
Figure 5B:
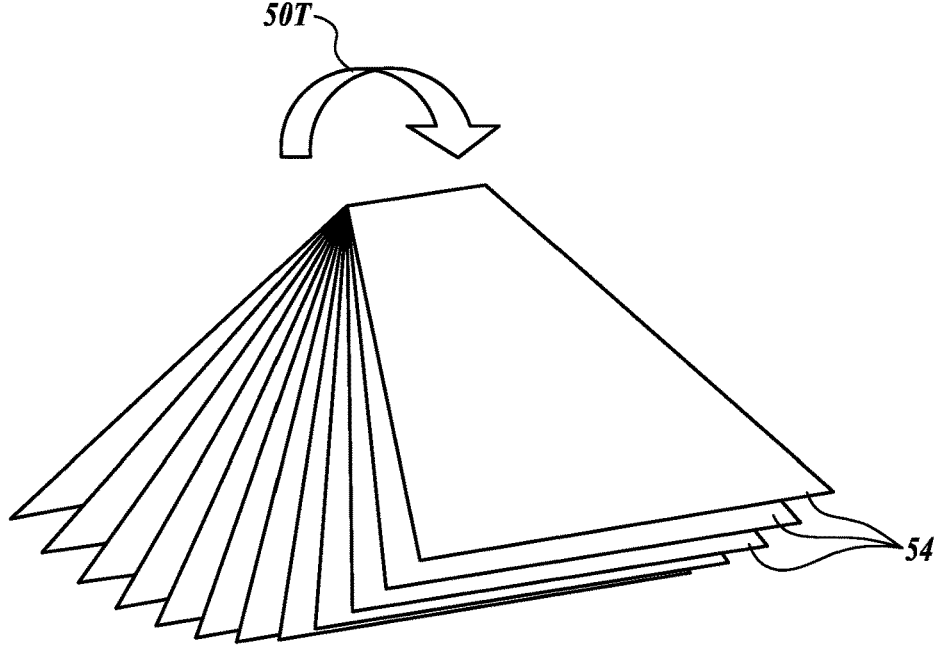
Figure 5C:
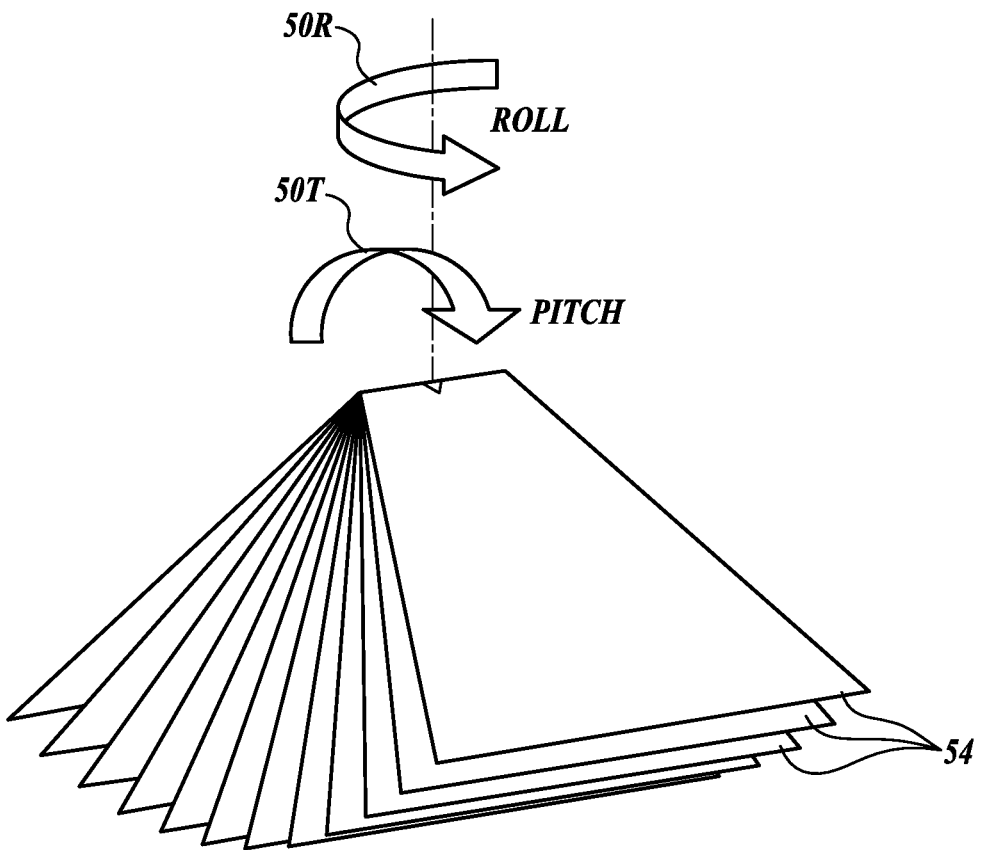

FIGS. 5A-5C show ultrasound planes transmitted in several rotation and tilting angles in accordance with an embodiment of the present technology. In particular, FIG. 5A illustrates ultrasound 54 transmitted in different rotational directions (rotational planes) 50R, and FIG. 5B illustrates ultrasound 54 transmitted in different tilt planes 50T. In some embodiments, direction of the transmitted and/or received ultrasound may be controlled by phased array elements or mechanical motors of the ultrasound probe 50. FIG. 5C shows that tilt (also referred to as a pitch) and rotation can be combined to expand the field of view.

Figure 6:
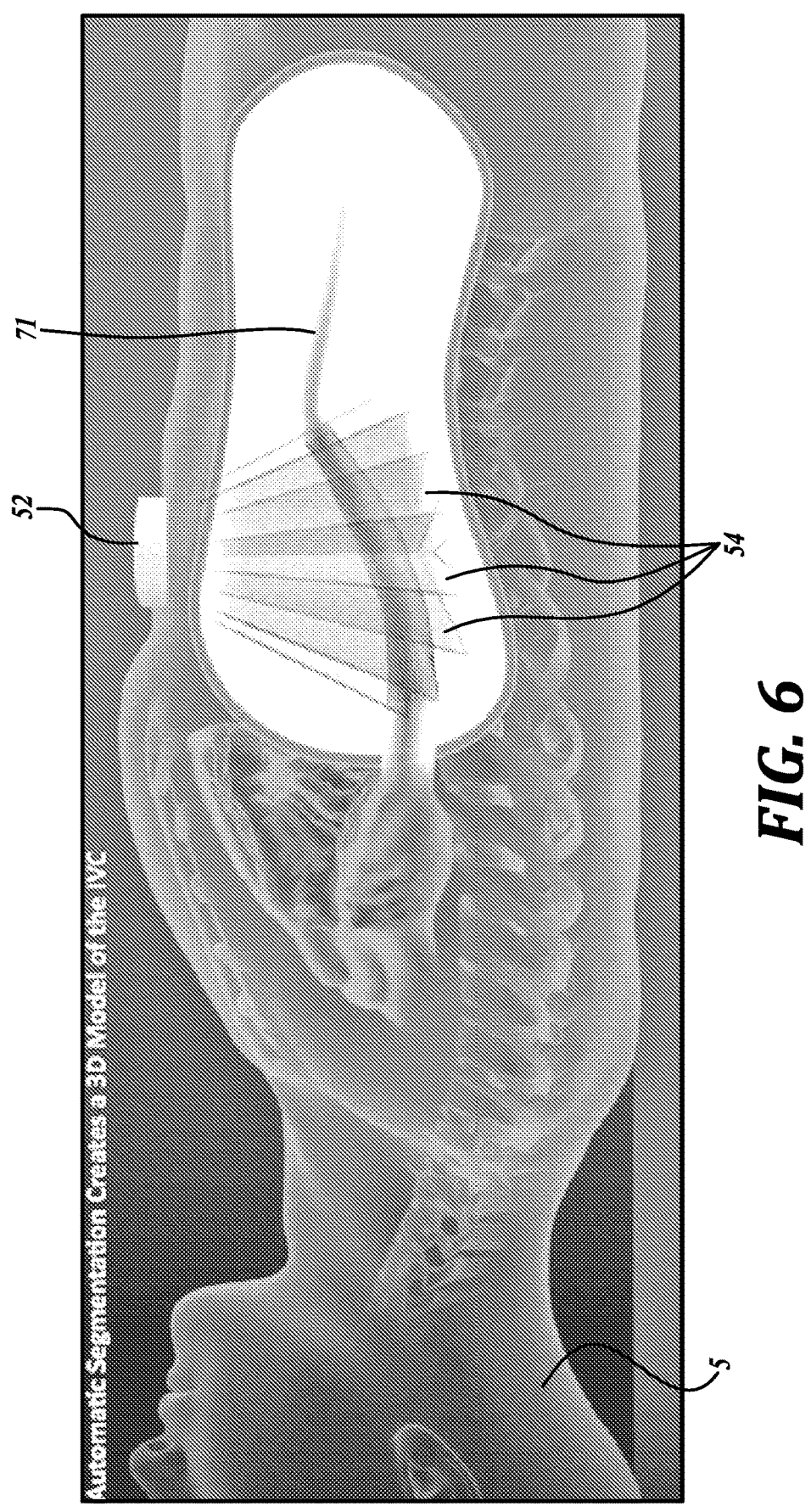
FIG. 6 is a side view of an ultrasound probe placement over a patient in accordance with an embodiment of the present technology.

FIG. 6 is a side view of an ultrasound probe placement over a patient in accordance with an embodiment of the present technology. In operation, the ultrasound probe 50 (e.g., a phased array probe) transmits ultrasound toward the IVC 71 as a set of ultrasound planes 54 that are offset by a rotational increment. The transmitted ultrasound is reflected off the target and then acquired by the receiver part of the transceiver 50. In some embodiments, the acquired ultrasound images are automatically analyzed to: 1) locate the IVC or other target vessel; 2) gain a coarse image of the IVC or other target vessel, 3) sharpen the image of the IVC or other target vessel, and 4) output the image to an image analysis software.

The system parameters may include: range of focus, depth of focus, gain, time-gain compensation, etc. Movements of the harness (if, for example, motorized) may be left to a pre-trained control system for adjustment until the IVC is properly identified. In some embodiments, artificial intelligence and machine learning may guide the initial placement to assure the target vessel is in the field of view.

Once the patient's IVC is located, ultrasound images are captured and uploaded to an image analysis program. Such computer program may be an implementation of a trained machine learning algorithm capable of identifying image features and producing measurement values associated with these image features. The algorithms may be trained with a set of images that were obtained using the harness system with manual measurements.

In different embodiments, the system can also work with body vessels other than the IVC. Therefore, even with smaller vessels the system may be precise enough to make the determinative measurements.

Figure 7A:
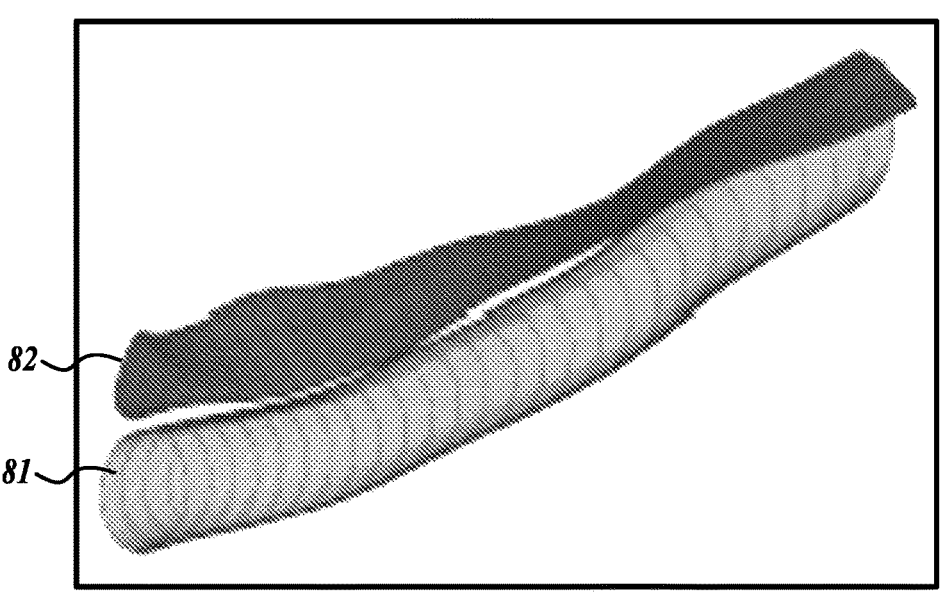
FIGS. 7A and 7B show carotid and jugular blood vessel during inhale and exhale phases of patient's breathing in accordance with an embodiment of the present technology.
Figure 7B:
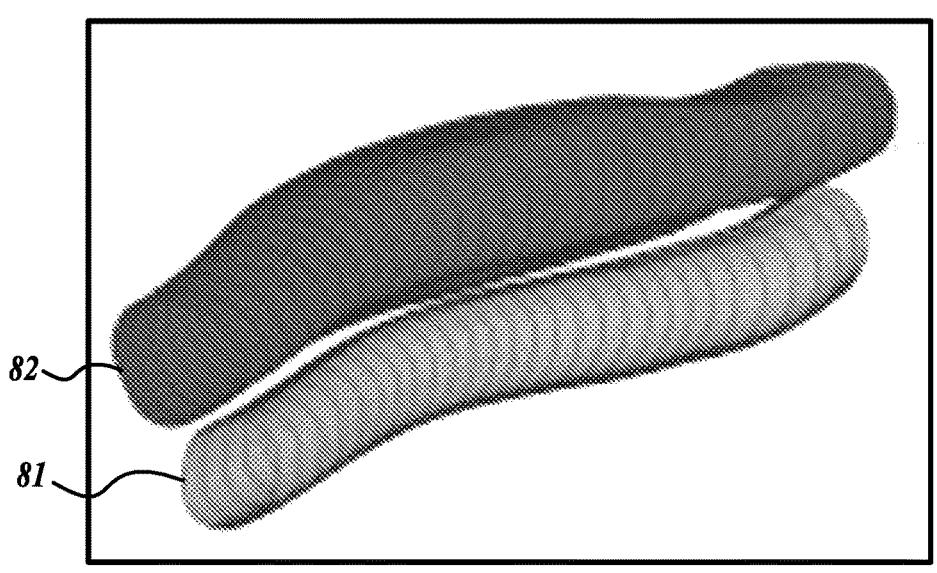

FIGS. 7A and 7B show carotid blood vessel 81 and jugular blood vessel 82 during the inhale and exhale phases of patient's breathing in accordance with an embodiment of the present technology. In particular, FIG. 7A corresponds to the inhale phase of the breathing cycle (also referred to as the inspiration phase), when the patient's diaphragm moves down, abdominal cavity shrinks, pressure increases and the jugular vein 82 partially collapses. FIG. 7B corresponds to the exhale phase of the breathing cycle (also referred to as the expiration phase), when the patient's diaphragm moves up, abdominal cavity expands, pressure decreases and the jugular vein 82 expands. The shape of the carotid and jugular vessels is shown as a 3D image for illustration. However, as further explained below with reference to FIGS. 8A and 8B, a 3D image reconstruction of these blood vessels may not be necessary for determining blood level of the patient, thus simplifying the inventive technology.

Figure 8A:
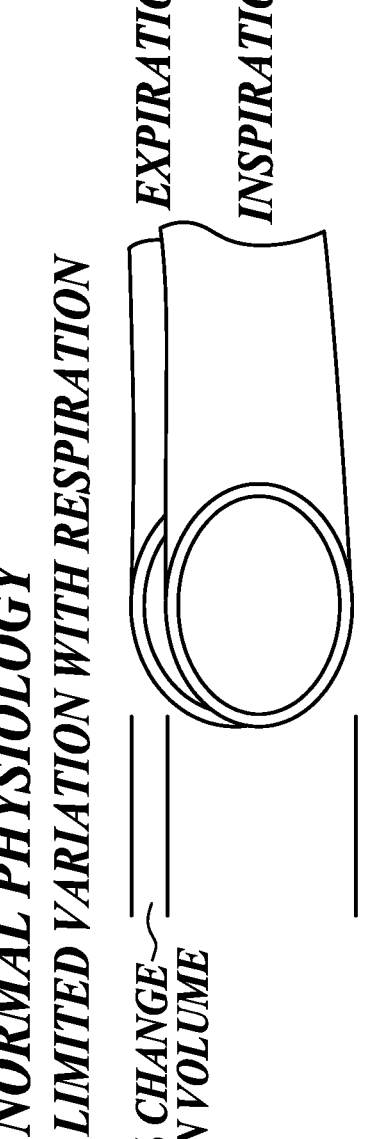
FIGS. 8A and 8B show IVC's change in volume during expiration and inspiration phases of patient's breathing in accordance with an embodiment of the present technology.
Figure 8B:
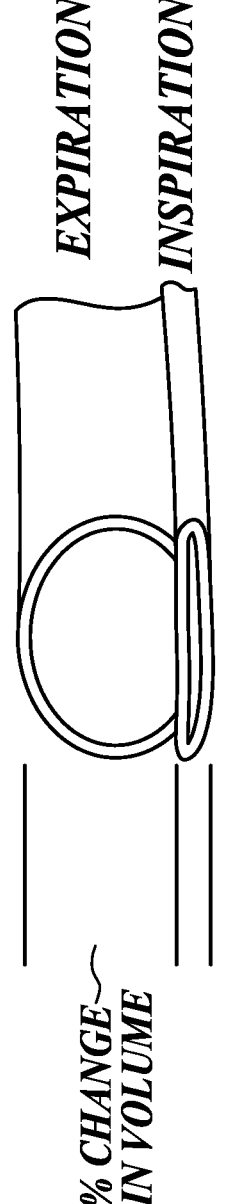

FIGS. 8A and 8B show IVC's change in volume during the expiration and inspiration phases of patient's breathing in accordance with an embodiment of the present technology. In particular, FIG. 8A shows the IVC for a patient with a "normal" physiology. For such a patient, the change in IVC's volume is relatively low as a percentage ratio between the larger, expiration driven volume of the IVC and the smaller, inspiration driven volume of the IVC. Such percentage change in volume may be determined as $D_{inspiration}/(D_{expiration}-D_{inspiration})$. For a person with a normal physiology, the percentage change may in some embodiments correspond to 5-20%

FIG. 8B illustrates the IVC's change in volume for a patient having a low intravascular volume physiology indicating an acute need for blood transfusion or an infusion. For such a patient, the percentage change in IVC's volume between the expiration and the inspiration phases may be as high as 100% (complete collapse of the IVC).

Studies have indicated that different segments of population have different physiologies when it comes to the IVC's volume changes during different phases of the breathing cycle. While the volume changes may be different for different segments of population, it may be possible to classify the different segments when training a machine learning algorithm to determine whether a particular threshold for the percentage change is reached.

In some embodiments, training of machine learning algorithm relies on available large heterogenous adult patient databases of HIPAA compliant, de-identified venous ultrasound images. Video clips of the venous examination from individual studies can be randomly distributed to training, validation, and test datasets in, for example, 80:10:10 ratio. The number of images needed to train segmentation models for ultrasound may depend on several factors, including the resolution (size) of the image and complexity of the model; the complexity of the segmentation task (identifying vessels from tissue is generally a medium complexity task); and the heterogeneity of the data. In some embodiments, about 500 studies may suffice to adequately train artificial intelligence algorithms. In the context of this inventive technology, a training dataset refers to a sample of data used to fit the deep learning model. The validation dataset refers to a set of separate data used to evaluate a model performance after each iteration of training. The test dataset refers to a separate set of data used to provide a final assessment of model performance.

In some embodiments, to perform the segmentation, computer vision methods are used for image filtering and deep learning models are used for segmentation. In particular, the inventors have found that U-Net-based models 6 works well in some segmentation scenarios. To perform an assessment of volume status from the segmented vein, the method may assess whether the vein decreases in caliber across the frames of the video (as the patient inspires). Metadata in the image file allows measurements of the caliber of the vein (e.g., $D_{expiration}$ and $D_{inspiration}$ in millimeters) across different frames. The baseline vein caliber in mm, and the change in vein caliber over frames, may be the same information used to derive the volume status from a trans-abdominal exam.

In some embodiments, performance metrics for a segmentation model include: 1) Dice score of model-predicted segmentations with manually labeled gold-standard segmentations; and 2) calculation of patient's volume status from the segmentations, compared to the clinically measured volume status (by right heart catheterization). Model performance metrics may include, but are not limited to, convergence plots, Dice scores, gradient-weighted class activation mapping as appropriate, and as also used with metrics for neural network model evaluation. Different models may be used for statistical comparison of automated volume status assessment to clinical volume status. Some examples of such models are Mann-Whitney U testing, Bland-Altman plots, and other metrics. Such models may be implemented on a general purpose computer (also referred to as personal computer, smart device, laptop, mainframe computer, controller, etc.).

Once trained per the above-described processes, the machine learning software may be capable of automatically identifying and measuring major venous structures from ultrasound images obtained by the hardware. Properly trained ultrasound system may make determinations as to whether the threshold percentage change in IVC's volume is reached (e.g., $D_{inspiration}(D_{expiration} D_{inspiration})$) without going through the process of reconstructing a 3D shape of the IVC during the inspiration/expiration phases.

Figure 9:
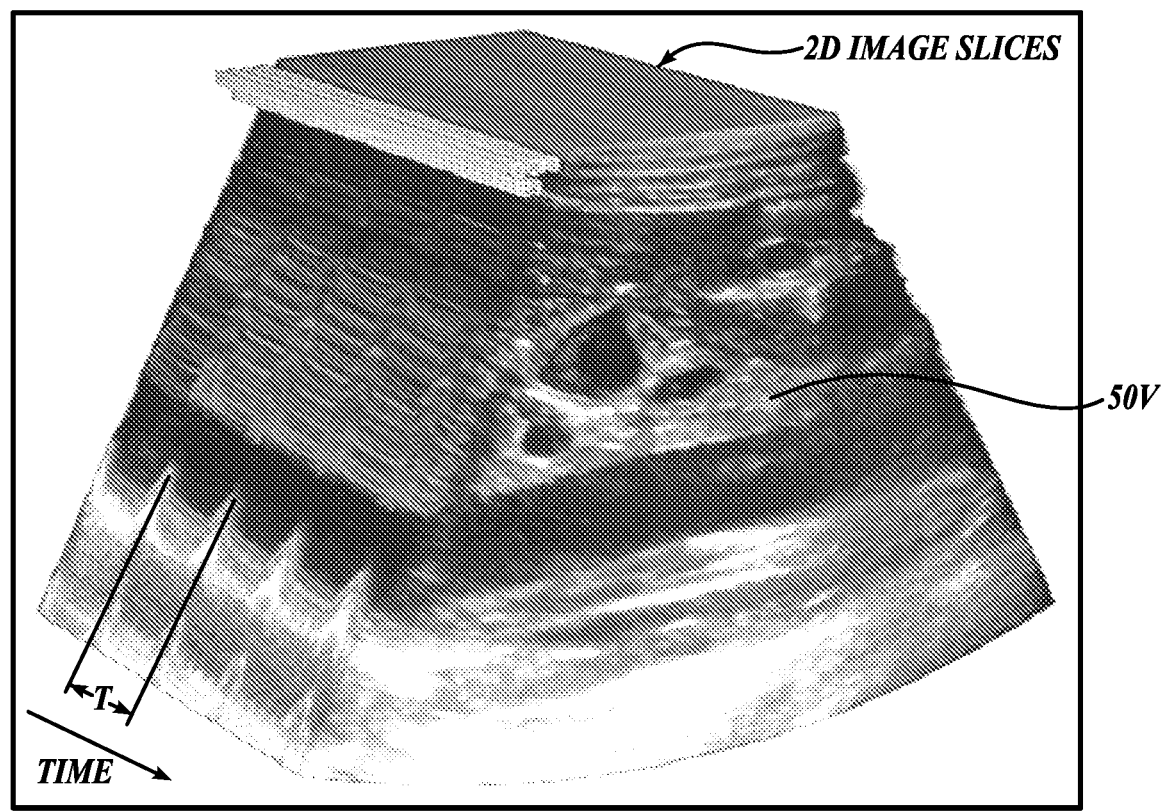
FIG. 9 shows volumetric M-mode display of the IVC in accordance with an embodiment of the present technology.

FIG. 9 shows volumetric M-mode display of the IVC in accordance with an embodiment of the present technology. M-mode (motion mode) ultrasound is an imaging method that records changes in depth of anatomic structures as a function of time. A known application of M-mode ultrasound is the measurement of the motion of the walls and valves of the heart. In some embodiments of inventive technology, spatial coverage of the M-mode is expanded to include the lateral direction of an ultrasound image plane (3D M-mode) plus cyclical spatial scanning by either tilt (pitch) or rotation (roll) of the imaging plane (4D M-mode). The illustrated example of such M-mode imaging 50V is a collection of 2D image slices arranged along a time axis, collectively representing a 3D image where the dimensions are space (two axes) and time (one axis). In a more general sense, which is difficult to illustrate in a drawing, a 4D M-mode may be constructed by arranging 3D images (total of three axes) along the time axis (one axis). Furthermore, scanning with cyclical changes in both tilt and rotation directions may produce a 5D M-mode data set, the dimensions being the depth and lateral image locations, tilt, rotation angle, and time.

Figure 10A:
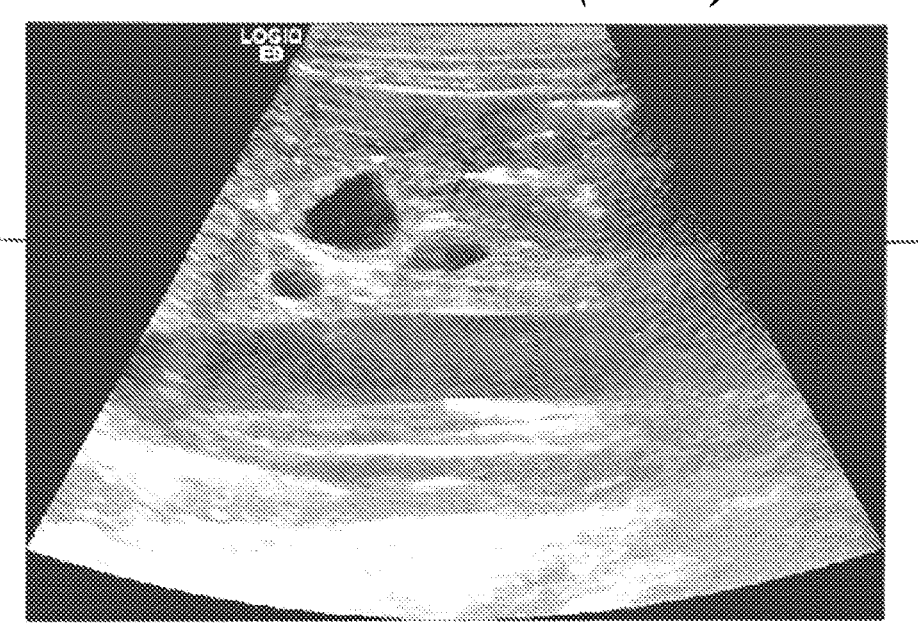
FIGS. 10A, 10B, 10C and 10D show different slices of M-mode display shown in FIG. 9.
Figure 10B:
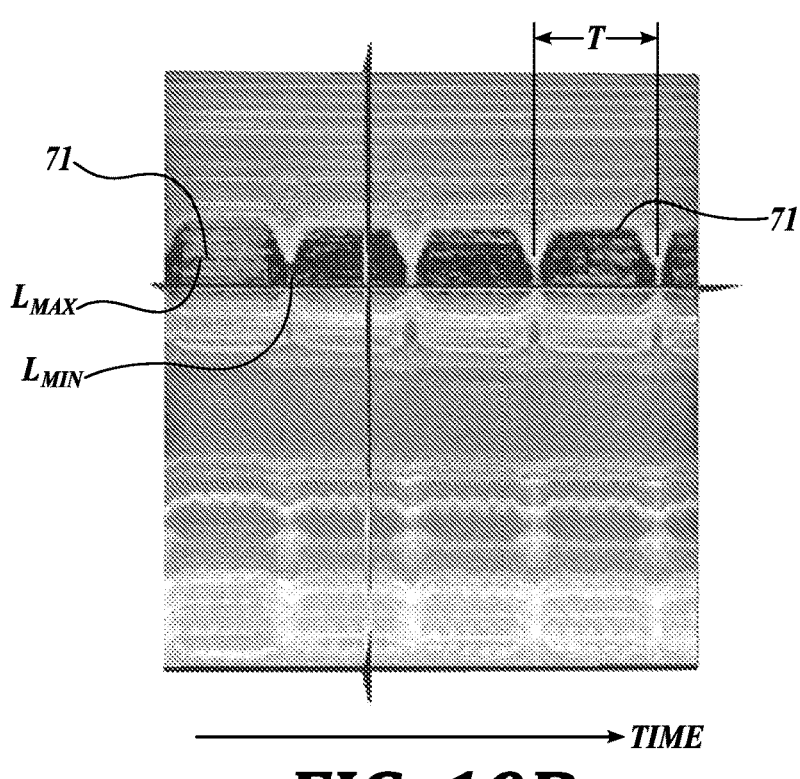
Figure 10C:
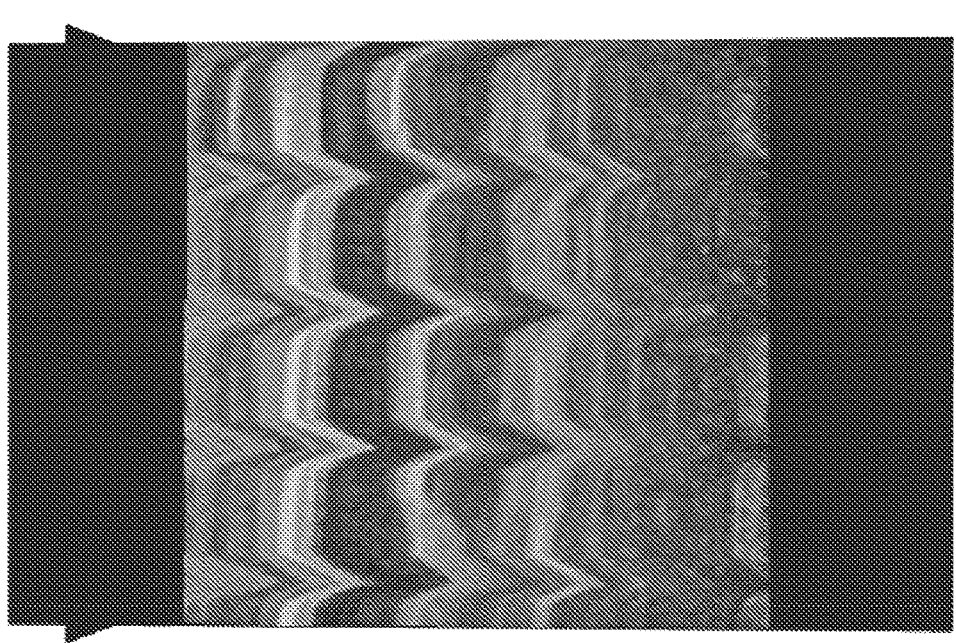
Figure 10D:
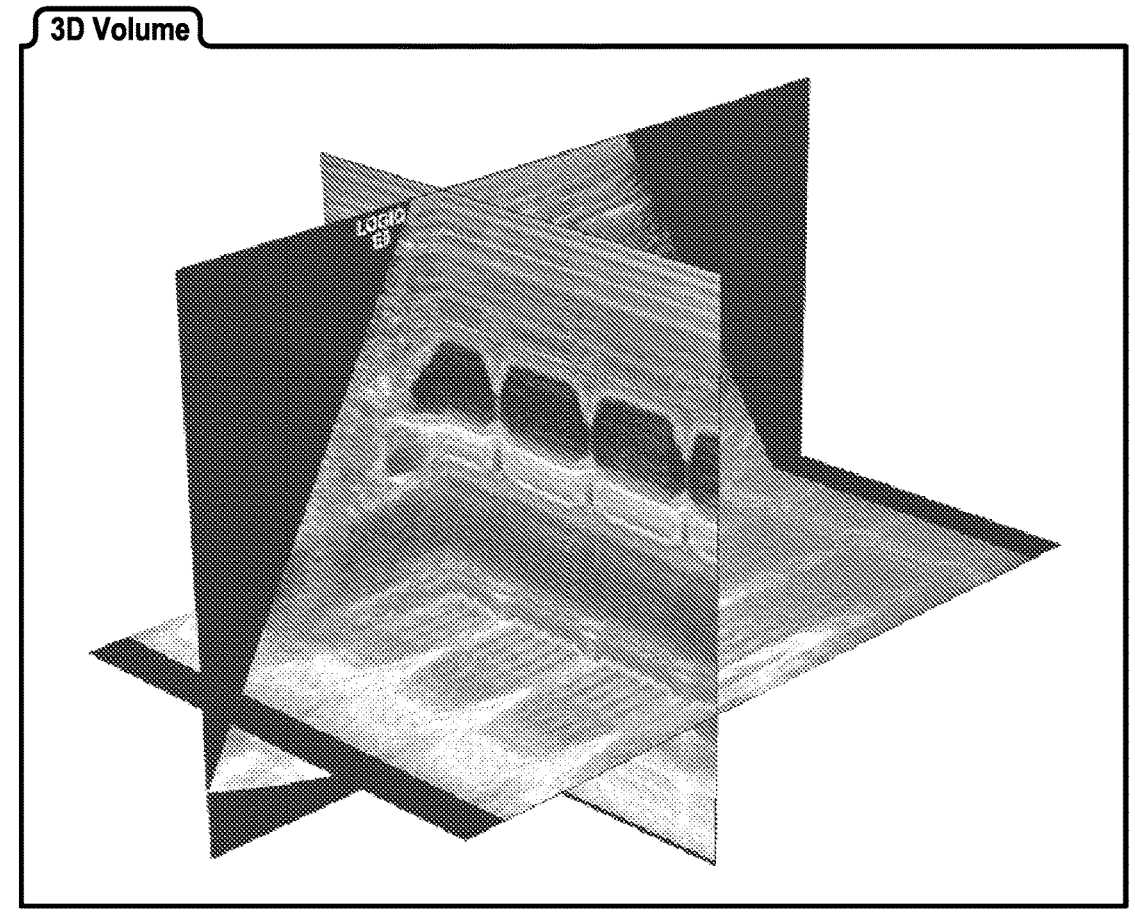

FIGS. 10A-10D show different slices of the M-mode display shown in FIG. 9. In particular, FIG. 10A illustrates 2D image along two spatial dimensions at a fixed time of the 3D image shown in FIG. 9. FIGS. 10B and 10C illustrate a 2D image along one spatial dimension (e.g., depth or lateral dimension) and time dimension. FIG. 10D illustrates several intersecting 2D slices taken over different dimensions.

Here, a breathing cycle has a duration of T. Therefore, during the breathing cycle T, the diameter of the IVC changes from its maximum diameter (or other characteristic caliber dimension) $L_{MAX}$ to its minimum diameter $L_{MIN}$. Therefore, using the M-mode slice in FIG. 10B it is possible to ascertain collapsibility of the IVC 71 (or other target vessel) without full 3D reconstruction of the shape and size of the IVC. Instead, a simple automated guidance signal based on ultrasound data may direct an operator to place the device on the skin over a vein of interest. The automated repetitive volume scan (e.g., using ultrasound tilt and/or rotation) then provides spatial coverage to capture the vein size data within the integrated field of view. The spatial scanning protocol eliminates the need to precisely place a single 2D image plane with an optimized view of the vessel of interest.

Figure 11:
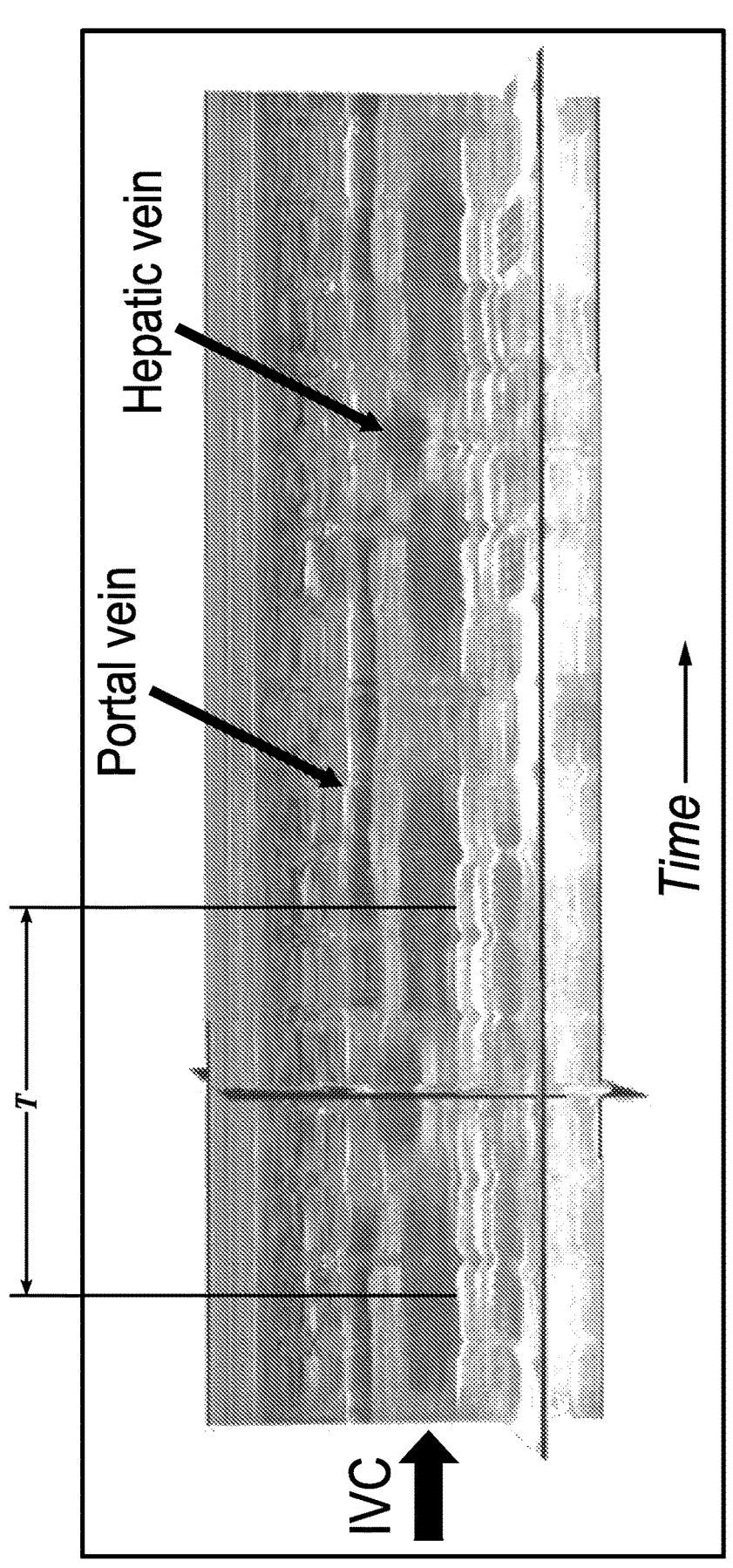
FIG. 11 shows a long-axis tilt scan view of a 4D M-mode display in accordance with an embodiment of the present technology.
Figure 12:
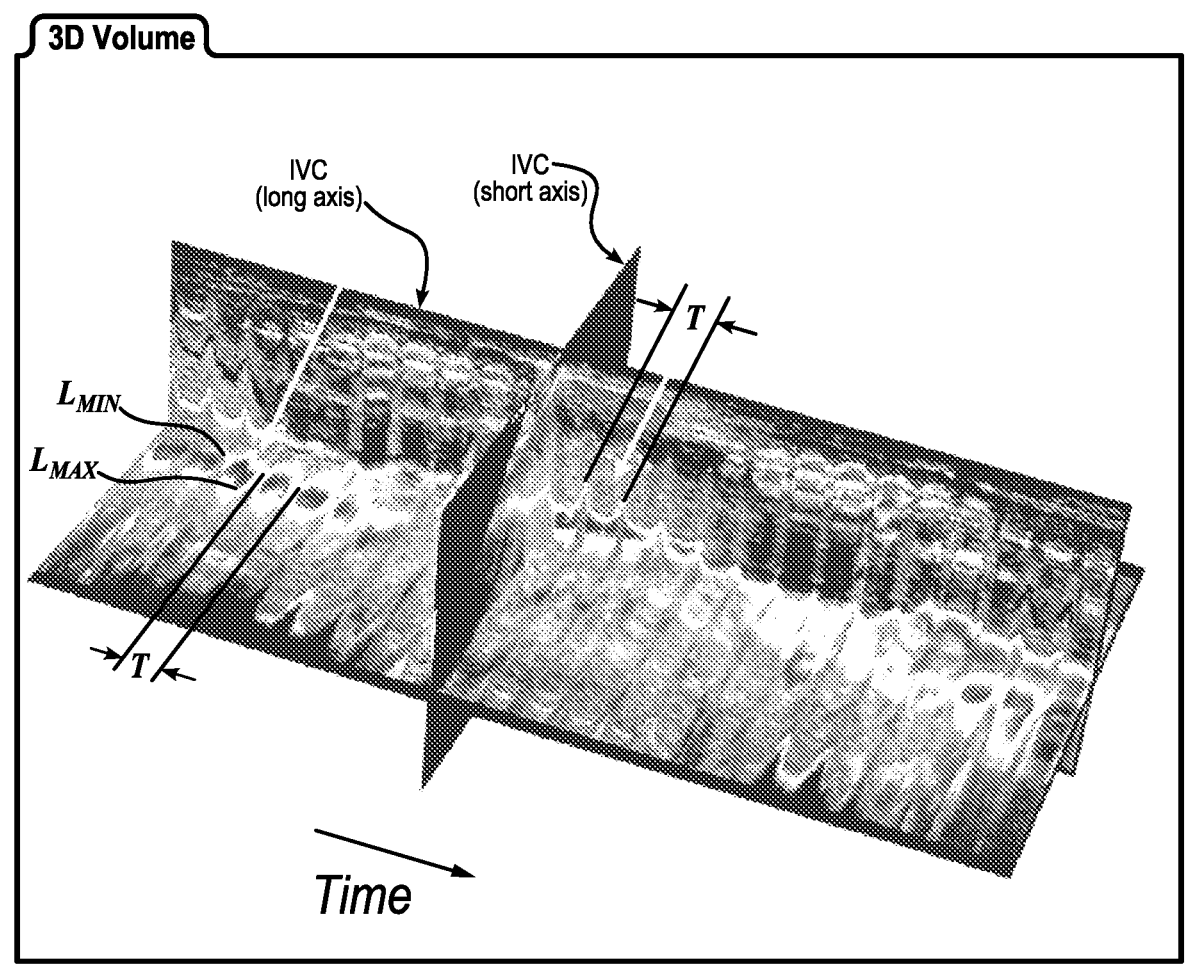
FIG. 12 shows a rotation scan view of a 4D M-mode display in accordance with an embodiment of the present technology.

FIGS. 11 and 12 show different views of a 4D M-mode display in accordance with an embodiment of the present technology. In particular, FIG. 11 shows a long-axis tilt scan views of a 4D M-mode display and FIG. 12 shows a rotation scan view of a 4D M-mode display. FIG. 12 shows isolated 2D images (slices) of a 3D volume taken along IVC's long axis (axial direction) and IVC's short axis (radial direction). These 2D slices correspond to different times of acquisition, where T is breathing period of the patient. By acquiring ultrasound image for an extended period of time (e.g., several multiples of T), the target vein is interrogated repeatedly in the scan volume at different points in the respiratory cycle. Based on the images along, for example long axis, $L_{MIN}$ (e.g., $D_{inspiration}$) and $L_{MAX}$ (e.g., $D_{expiration}$) can be determined at different times. Therefore, a percentage change in volume may be determined as $D_{inspiration}$ ($D_{expiration}$ $D_{inspiration}$) based on properly trained artificial intelligence, and without needing highly skilled medical technicians or physicians. Such determination may be based on a movement of the boundary of IVC, without determining a full 3D outline of the IVC. In the context of this disclosure, the term IVC is used to represent other veins or fluid vessels in a human body. A non-limiting example of such vein is a hepatic vein shown in FIG. 11. There are several options for slice extraction, including at angles perpendicular to the vessel axis. For the rotation scan of FIG. 12, the 'Long' and 'Short' labels show the times when the probe is oriented such that these views of the vein are acquired.

Figure 13A:
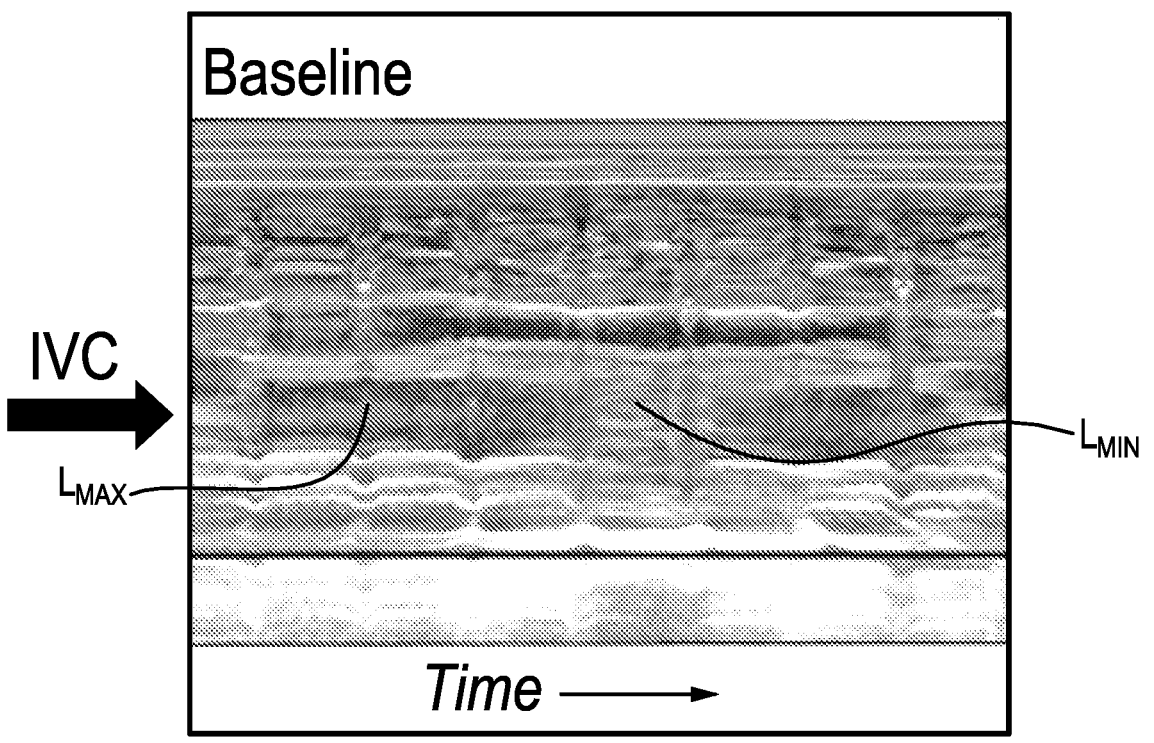
FIGS. 13A-13C show baseline, late shock and late resuscitation views extracted from a 4D M-mode display in accordance with an embodiment of the present technology.
Figure 13B:
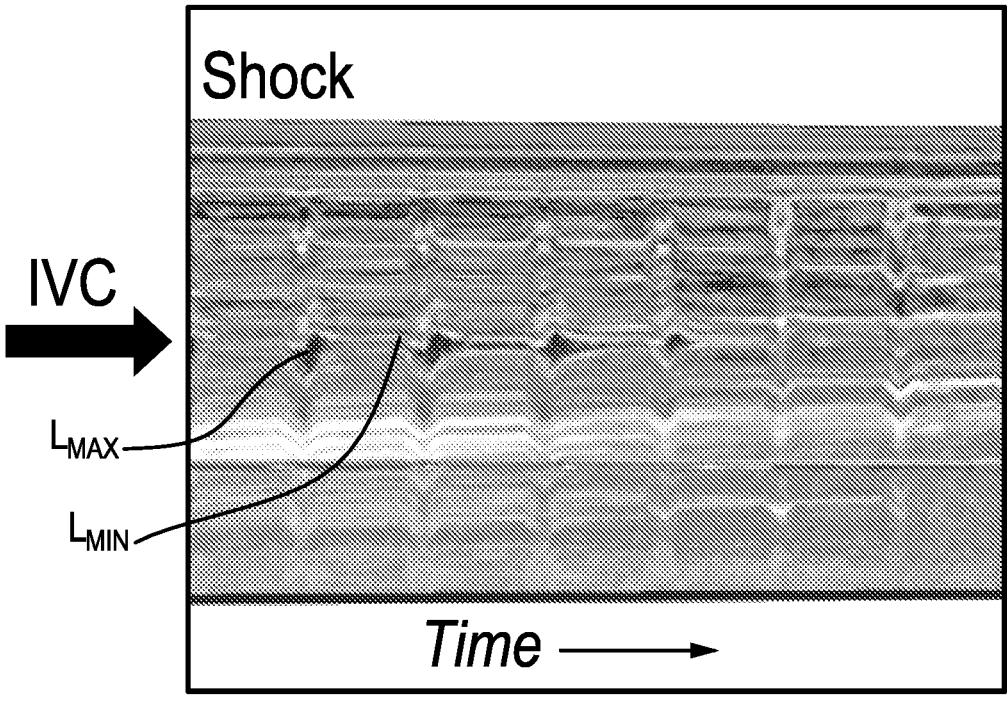
Figure 13C:
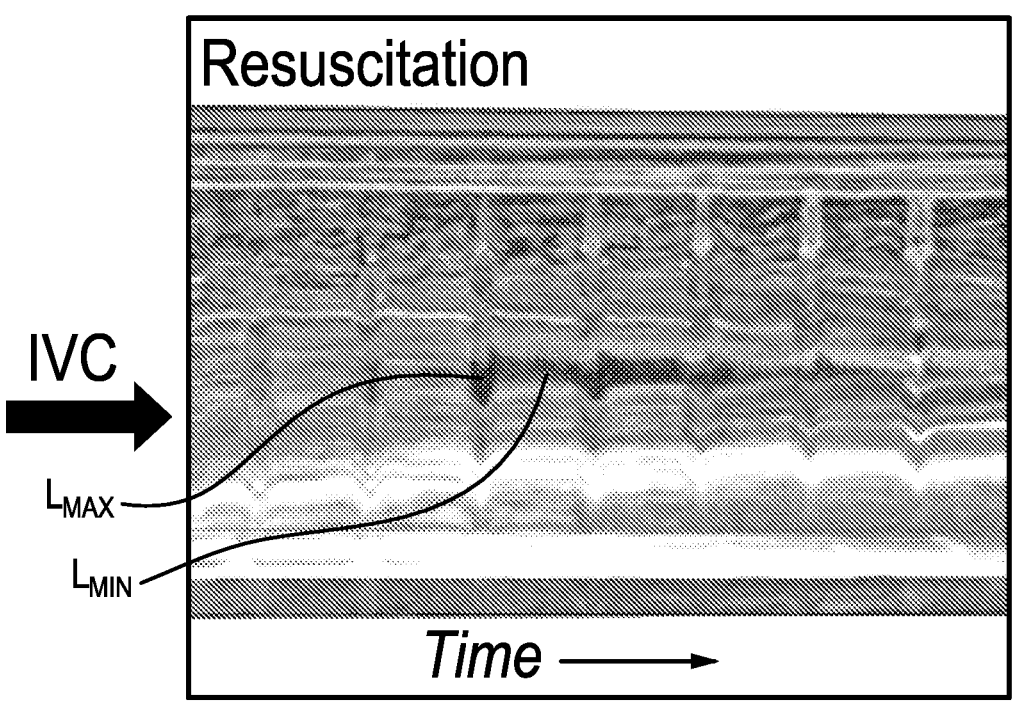

FIGS. 13A-13C show baseline, late shock and late resuscitation views extracted from a 4D M-mode display in accordance with an embodiment of the present technology. In each Figure, the horizontal axis represents time in a duration of several breathing periods T. The vertical axis shows features of the IVC as a composite picture acquired along a chosen plane at different times. The patient in FIGS. 13A-13C is a test animal.

FIG. 13A shows a baseline case where IVC is characterized by a relatively large maximum dimension ($L_{MAX}$ or $D_{expiration}$) of the IVC, indicating an appropriate blood level of the patient. FIG. 13B shows the patient in the state of shock that is characterized by a relatively small $L_{MAX}$ dimension of the IVC even during the expiration cycle. In at least some embodiments, such relatively small $L_{MAX}$ dimension of the IVC indicates low blood level.

FIG. 13C shows the patient during the resuscitation, when the patient is brought back from the prior state of shock. Here, the $L_{MAX}$ dimension of the IVC becomes larger than it was during the state of shock. Such increase in the $L_{MAX}$ dimension may signify addition of blood or other fluids to the patient.

Figure 14:
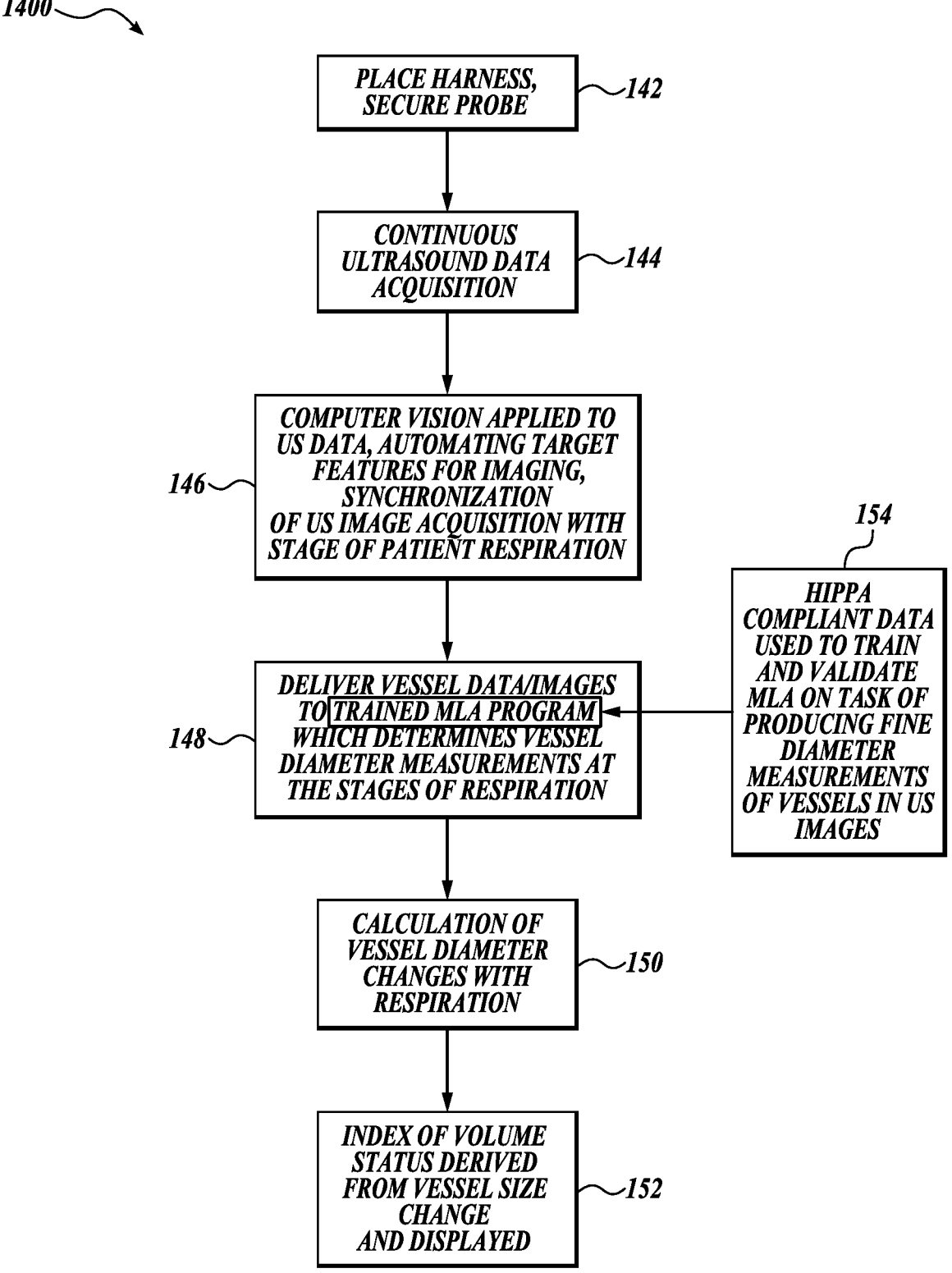
FIG. 14 is a flowchart of a method for determining fluid volume in a patient in accordance with an embodiment of the present technology.

FIG. 14 is a flowchart of a method for determining fluid volume in a patient in accordance with an embodiment of the present technology. In some embodiments, the method may include additional steps or may be practiced without all steps illustrated in the flow chart.

The method starts in block 142 where a technician places a harness 57 on the patient to secure the ultrasound probe 50 in place. In block 144, ultrasound is transmitted toward the patient, and reflected ultrasound is received and acquired. As explained above, data may be transmitted by the ultrasound transceiver 50 that is a phased array capable of transmitting/receiving ultrasound in different directions (e.g., rotation and tilt directions). In other embodiments, the ultrasound transmitter may be separate from the ultrasound receiver. In some embodiments, the ultrasound transmitter may be a single probe with in-plane mechanical scanning and mechanical tilt/rotation. In other embodiments, the ultrasound transceiver 50 may be an array (phased, linear, and/or curvilinear) with mechanical tilt/rotation. In some embodiments, the ultrasound transceiver 50 may be a 2D matrix array, i.e., having all electronic scanning and no mechanical motors. In other embodiments, the ultrasound transceiver 50 may be a 2D matrix array plus mechanical tilt/rotation to expand the field of view. Data may be continuously acquired, generally over several breathing cycles of the patient.

In some embodiments, the method may use positioning feedback by AI, where the real-time image is evaluated by automated software and simple feedback signals are provided to the user to signify: 1) direction to shift the probe and 2) clear signal when good positioning is achieved.

In block 146, computer vision is applied to ultrasound (US) data for, for example, automating acquisition of the target features for imaging. Data acquisition may be synchronized with breathing (respiration) cycles of the patient, such that different images are tagged to a particular stage of patient's respiration (i.e., inspiration and expiration stages). In some embodiments, the analysis is gated by respiration and the image acquisition is continuous.

In block 154, artificial intelligence is trained through machine learning algorithms (MLAs), and results are validated using HIPPA compliant data. Trained artificial intelligence may be capable of measuring body vessel diameters from the provided images without reconstructing a 3D shape of the body vessel.

In block 148, patient data acquired in block 146 are provided to the trained MLA programs (i.e., artificial intelligence) for the determination of vessel diameter at different stages of respiration. The images may be 3D reconstructions, still ultrasound images, or M-mode ultrasound images.

In block 150, changes in vessel diameter are determined for different phases of respiration. As explained above, ultrasound image acquisition and/or analysis may be synchronized with different phases of respiration.

In block 152, index of vessel's volume status is derived from the vessel diameter that was determined in block 150. In some embodiments, vessel's volume status may be expressed as $D_{inspiration}$ ($D_{expiration}$–$D_{inspiration}$). The resulting value may be displayed and compared to one or more predetermined thresholds that determine if an intervention (e.g., blood transfusion) is needed and, if so, in what degree. In some embodiments, the comparison of the vessel's volume to predetermined threshold and/or determination of suitable intervention may be done by artificial intelligence.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

Many embodiments of the technology described above may take the form of computer- or controller-executable instructions in a non-volatile memory, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A system for monitoring a blood volume of a patient, the system comprising:
   an ultrasound transmitter configured for emitting an ultrasound toward a target blood vessel of the patient;
   an ultrasound receiver configured for receiving the ultrasound reflected from the target blood vessel of the patient; and
   a controller configured for:
      obtaining a 5D M-mode ultrasound dataset of the target blood vessel, wherein dimensions of the 5D M-mode ultrasound dataset are a two-dimensional image plane comprising a depth dimension and a lateral location dimension, time, a tilt angle, and a rotation angle;
      determining an expanded state of the target blood vessel based on the 5D M-mode ultrasound dataset of the target blood vessel and a machine learning algorithm without determining a 3D shape representing a volume of the target blood vessel;
      determining a collapsed state of the target blood vessel based on the 5D M-mode ultrasound dataset of the target blood vessel and the machine learning algorithm without determining the 3D shape representing the volume of the target blood vessel;
      determining a ratio of the collapsed state and the expanded state of the blood vessel; and
      determining the blood volume of the patient based on the ratio of the collapsed state and the expanded state of the blood vessel.

2. The system of claim 1, wherein the determining the expanded state of the blood vessel is synchronized with an expiration cycle of patient's breathing, and the determining of the collapsed state of the blood vessel is synchronized with an inspiration cycle of the patient's breathing.

3. The system of claim 1, wherein the controller is further configured for determining whether the patient requires a blood transfusion.

4. The system of claim 3, wherein the machine learning algorithm classifies different segments of a population to determine whether the ratio of the collapsed state and the expanded state of the blood vessel is below a predetermined threshold for a particular segment of the population.

5. The system of claim 1, wherein the blood vessel is an inferior vena cava (IVC).

6. The system of claim 1, wherein the ultrasound is transmitted toward the target blood vessel in a plurality of rotational planes and tilt planes.

7. The system of claim 1, wherein the ultrasound transmitter is a phased array ultrasound transmitter.

8. The system of claim 1, wherein the controller is further configured for extracting 2D image slices from the 5D M-mode images.

9. A method for monitoring a blood volume of a patient, the method comprising:
   emitting an ultrasound toward a target blood vessel of the patient by an ultrasound transmitter;
   receiving the ultrasound reflected from the target blood vessel of the patient by an ultrasound receiver;
   obtaining a 5D M-mode ultrasound dataset of the target blood vessel, wherein dimensions of the 5D M-mode ultrasound dataset are a two-dimensional image plane comprising a depth dimension and a lateral location dimension, time, the tilt angle, and the rotation angle;
   determining an expanded state and a collapsed state of the blood vessel based on the 5D M-mode ultrasound dataset of the target blood vessel and a machine learning algorithm without determining the 3D shape representing a volume of the target blood vessel;
   determining a ratio of the collapsed state and the expanded state of the blood vessel; and
   determining the blood volume of the patient based on the ratio of the collapsed state and the expanded state of the target blood vessel.

10. The method of claim 9, further comprising:
   synchronizing the determining the expanded state of the blood vessel with an expiration cycle of patient's breathing, and
   synchronizing the determining of the collapsed state of the blood vessel with an inspiration cycle of the patient's breathing.

11. The method of claim 9, further comprising determining whether the patient requires a blood transfusion based on the ratio of the collapsed state and the expanded state of the blood vessel being below a predetermined threshold.

12. The method of claim 9, wherein the blood vessel is an inferior vena cava (IVC).

13. The method of claim 9, wherein the machine learning algorithm classifies different segments of a population to determine whether the ratio of the collapsed state and the expanded state of the blood vessel is below a predetermined threshold for a particular segment of the population.

14. The method of claim 9, wherein the ultrasound is transmitted toward the target blood vessel in a plurality of rotational planes and tilt planes by the ultrasound transmitter that is a phased array ultrasound transmitter.

15. The method of claim 9, further comprising extracting 2D image slices from the 5D M-mode images.

16. The method of claim 15, wherein the 2D image slices are extracted along a time axis of the 5D M-mode images.

17. The method of claim 16, wherein generating the 5D M-mode image of the blood vessel comprises extracting 2D image slices at multiple locations in the lateral direction of the 5D M-mode image.

18. The method of claim 9, further comprising scanning the depth dimension, the lateral location dimension, the tilt, the rotation, and time.

* * * * *